United States Patent
Davis et al.

(10) Patent No.: US 10,834,942 B2
(45) Date of Patent: Nov. 17, 2020

(54) YEAST AND BACTERIAL PROBIOTICS COMBINATIONS AND METHODS OF USE TO IMPROVE SWINE PRODUCTION

(71) Applicants: Church & Dwight Co., Inc., Ewing, NJ (US); NutriQuest, LLC, Mason City, IA (US)

(72) Inventors: Mari Ellen Davis, Waukesha, WI (US); Kim Friesen, Carthage, IN (US); Thomas G. Rehberger, Wauwatosa, WI (US); Ran Song, Eden Prairie, MN (US)

(73) Assignee: Church & Dwight Co., Inc., Princeton, NJ (US)

( * ) Notice: Subject to any disclaimer, the term of this patent is extended or adjusted under 35 U.S.C. 154(b) by 59 days.

(21) Appl. No.: 15/950,750

(22) Filed: Apr. 11, 2018

(65) Prior Publication Data
US 2018/0289038 A1 Oct. 11, 2018

Related U.S. Application Data

(60) Provisional application No. 62/484,058, filed on Apr. 11, 2017.

(51) Int. Cl.
| | | |
|---|---|---|
| A23K 10/18 | (2016.01) |
| A23K 10/30 | (2016.01) |
| C12N 1/20 | (2006.01) |
| A23K 50/30 | (2016.01) |
| C12R 1/07 | (2006.01) |
| C12R 1/865 | (2006.01) |
| A61K 36/064 | (2006.01) |
| A61K 35/742 | (2015.01) |

(52) U.S. Cl.
CPC ............ *A23K 10/18* (2016.05); *A23K 10/30* (2016.05); *A23K 50/30* (2016.05); *A61K 35/742* (2013.01); *A61K 36/064* (2013.01); *C12N 1/20* (2013.01); *C12R 1/07* (2013.01); *C12R 1/865* (2013.01)

(58) Field of Classification Search
None
See application file for complete search history.

(56) References Cited

U.S. PATENT DOCUMENTS

| | | | |
|---|---|---|---|
| 8,021,654 B2* | 9/2011 | Rehberger | A61K 35/74 424/93.1 |
| 8,506,951 B2* | 8/2013 | Rehberger | A61K 35/74 424/93.1 |
| 2014/0037582 A1 | 2/2014 | Romero et al. | |

FOREIGN PATENT DOCUMENTS

| | | | |
|---|---|---|---|
| WO | WO 2012/110776 A2 | 8/2012 | |
| WO | WO-2012110776 A2 * | 8/2012 | ............... C12N 1/20 |
| WO | WO 2017/205645 A1 | 11/2017 | |

OTHER PUBLICATIONS

Baker, A., et al., "The effect of a *Bacillus*-based direct-fed microbial supplemental to sows on the gastrointestinal microbiota of their neonatal piglets," *J. Anim. Sci.*, 2013, vol. 91, pp. 3390-3399.
Barker, M., et al., Effects Of Bioplus 2B and Levucell SB on Weanling Pig Growth Performance and Fecal Shedding in Response to Oral Challenge With *Salmonella* Serovar Typhimuruim, Proceedings of the Kansas State University Swine Day, 2003, pp. 136-140.
Bass, B., et al., "Impact of a whole yeast product on sow, litter, and nursery performance," *Arkansas Anim Sci Dep Rep 2012*, 2013, pp. 104-115.
Buntyn, J., et al., "The Role of Direct-Fed Microbials in Conventional Livestock Production," *Annu. Rev. Anim. Biosci.*, 2016, vol. 4(1), pp. 335-355.
Chen, Y., et al., "Effects of Dietary *Bacillus*-based Probiotic on Growth Performance, Nutrients Digestibility, Blood Characteristics and Fecal Noxious Gas Content in Finishing Pigs," *Asian-Australasian Journal of Animal Sciences*, 2006, vol. 19(4), pp. 587-592.
Choi, J., et al., "Evaluation of multi-microbe probiotics prepared by submerged liquid or solid substrate fermentation and antibiotics in weaning pigs," *Livestock Science*, 2011 vol. 138(1), pp. 144-151.
Cui, C., et al., "Effects of dietary *Bacillus subtilis* on proportion of Bacteroidetes and Firmicutes in swine intestine and lipid metabolism," *Genetics and Molecular Research*, 2013, vol. 12, pp. 1766-1776.
Davis, M., et al., "Effect of a *Bacillus*-based direct-fed microbial feed supplement on growth performance and pen cleaning characteristics of growing-finishing pigs," *J. Anim. Sci.*, 2008, vol. 86, pp. 1459-1467.
Fahmy, M., et al., "Interrelations between some reproductive traits in swine," *Can. J. Anim. Sci.*, 1971, vol. 52, pp. 39-45.
Giang, H., et al., "Effects of supplementation of probiotics on the performance, nutrient digestibility and faecal microflora in growing-finishing pigs," *Asian-Aust. J. Aim. Sci.*, 2011, vol. 24, pp. 655-661.
Gomez, S., et al., "Combination of an enzymatically hydrolyzed yeast and yeast culture with a direct-fed microbial in the feeds of broiler chickens," *Asian-Aust J. Anim. Sci.*, 2012, vol. 25, pp. 665-673.
Hentges, D., "Chapter 5—Gut flora in disease resistance," In *Probiotics: The scientific basis*, 1992, pp. 87-110, ed. Chapman and Hall, London, UK.
Hong, H., et al., "The use of bacterial spore formers as probiotics," *FEMS Microbiology Reviews*, 2005, vol. 29, pp. 813-835.
Hu, Y., et al., "Effects of *Bacillus subtillis* KN-42 on growth performance, diarrhea and faecal bacterial flora of weaned piglets," *Asian Aust. J. Anim. Sci.*, 2014, vol. 27, pp. 1131-1140.

(Continued)

*Primary Examiner* — David W Berke-Schlessel
(74) *Attorney, Agent, or Firm* — Church & Dwight Co., Inc.

(57) ABSTRACT

The invention is directed to compositions and methods are disclosed for improving production of swine. In one embodiment the composition may include a combination of at least one of a biologically pure culture of *Bacillus* strains. The composition may comprise a *Saccharomyces cerevisiae* yeast product. Methods are disclosed for providing beneficial effects to swine and their offspring, including but not limited to improved performance of the swine.

31 Claims, 6 Drawing Sheets

(56) References Cited

OTHER PUBLICATIONS

Figure 1:
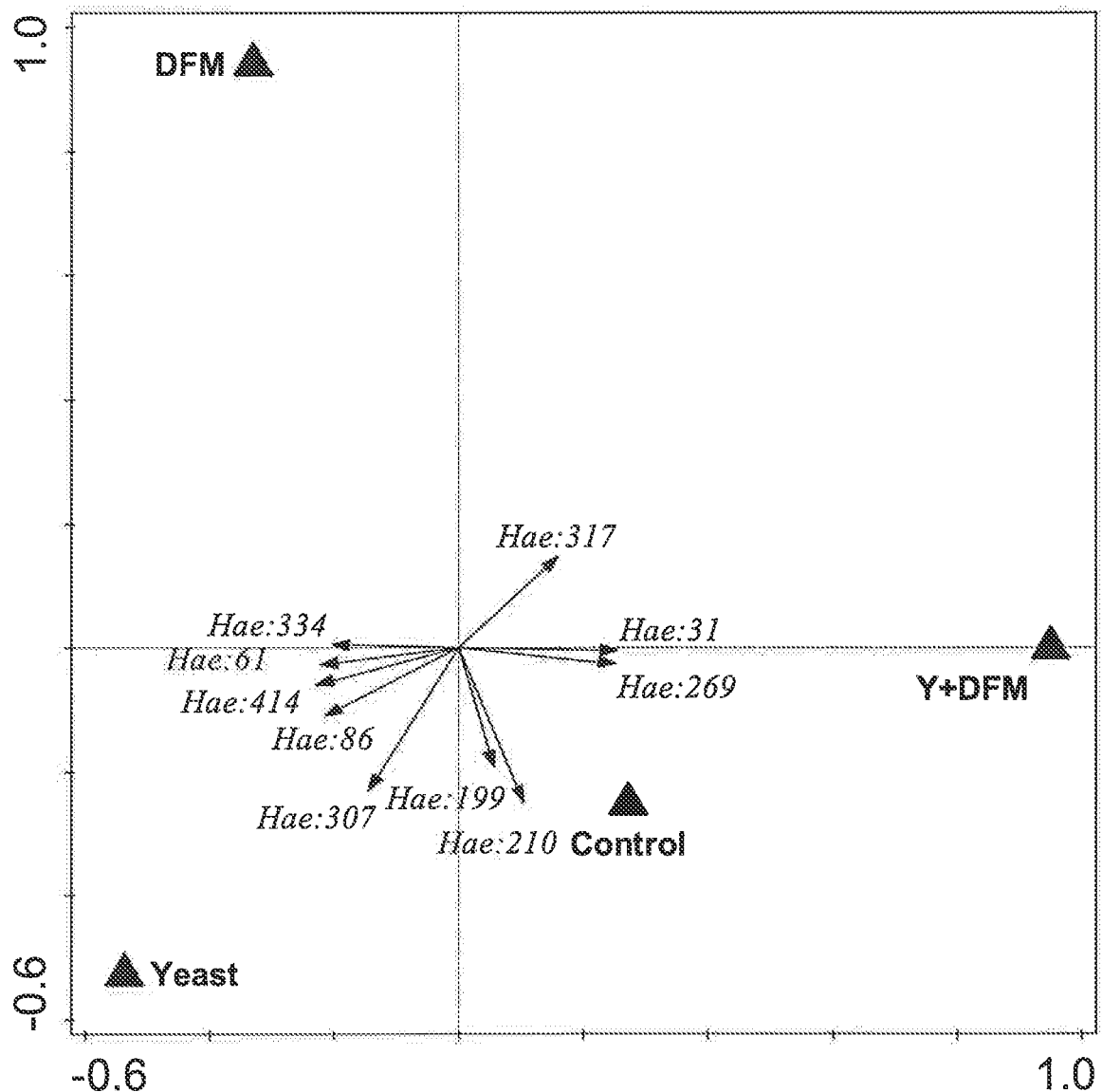

Jang, Y., et al., "Effects of live yeast supplementation to gestation and lactation diets on reproductive performance, immunological parameters and milk composition in sows," *Livestock sci.*, 2013, vol. 152, pp. 167-173.

Jurgens, M., et al., "The effect of dietary active dry yeast supplement on performance of sows during gestation-lactation and their pigs," *J. Anim. Sci.*, 1997, vol. 75, pp. 53-597.

Kim, S. et al., "Effect of supplementing *Saccharomyces cerevisae* fermentation product in sow diets on reproductive performance in a commercial environment," *Canadian journal of animal sciences*, 2010, vol. 9, pp. 2290-3232.

Lee, K., et al., "*Bacillus subtilis*-based direct-fed microbials augment macrophage function in broiler chickens," *Research in Veterinary Science*, 2011, vol. 91(3), pp. e87-e391.

Maruta, K., et al., "Effects of Bacillus subtilis C-3102 intake on fecal flora of sows and on diarrhea and mortality rate of their piglets," *Anim. Sci., Technol.*, 1996, vol. 67, pp. 403-409.

Min, B., et al., "The effect of Bacillus and active yeast complex supplementation on the performance, fecal Bacillus counts and ammonia nitrogen concentrations in weaned pigs," *J. Anim. Sci.*, 2003, vol. 82(Suppl. 1), p. 26, abstract.

Plante, P., et al., "Effect of supplementing the diet of lactating sows with NuPro® on sow lactation performance and piglet growth," *Canadian Journal of Animal Science*, 2011, vol. 91, pp. 295-300.

Soccol, C., et al., "The potential of probiotics: a review," *Food Technol. Biotechnol.*, 2010, vol. 48, pp. 413-434.

Veum, T., et al., "Effect of supplemental yeast culture in sow gestation and lactation diets on apparent nutrient digestibles and reproductive performance through one reproductive cycle," *J. Anim. Sci.*, 1995, vol. 73, pp. 1741-1745.

Zanello, G., et al., "Effects of dietary yeast stains on immunoglobulin in colostrum and milk of sows," *Vet. Immunology and Immunopathology*, 2012, vol. 152, pp. 20-27.

Lindemann, et al., "Benefits of Cel-Can®, an anzymatically hydrolyzed yeast product, for sows and weanling pigs," *American Association of Swine Veterinatians Annual Meeting: Implementing Knowledge*, 2010, pp. 183-186.

Cui, K., et al., "Effects of dietary supplementation with *Bacillus subtilis* and yeast culture on growth performance, nutrient digestibility, serum indices and faeces microbiota of weaned piglets," *Journal of Animal and Feed Sciences*, 2019, vol. 28, pp. 328-336.

Davis, E., et al., "Administration of a *Bacillus* probiotic to sows improves growth response and health of their progeny after weaning," *J. Anim. Sci.*, 2020, vol. 98:Suppl. 2 (Abstract #268).

\* cited by examiner

YEAST AND BACTERIAL PROBIOTICS COMBINATIONS AND METHODS OF USE TO IMPROVE SWINE PRODUCTION

CROSS-REFERENCE TO RELATED APPLICATIONS

This application claims priority to U.S. Provisional Patent Application No. 62/484,058 filed Apr. 11, 2017; the entirety of which is incorporated by reference herein,

BIBLIOGRAPHY

Complete bibliographic citations of those references that are referred to herein by the first author's last name and year of publication in parentheses can be found in the Bibliography section, which precedes the claims.

FIELD OF THE INVENTION

The disclosure relates to compositions and methods for improving swine production. More particularly, the disclosure relates to compositions including *Bacillus* strains, *Saccharomyces cerevisiae* yeast and methods of formulating and using the same for improving swine production.

BACKGROUND

Enhancing sow productivity is key to improving cost of production and optimizing profitability of pigs marketed for meat. The disclosure provided herein demonstrates several combinations of yeast and probiotic bacteria to improve sow productivity, and wearied pig immunity and survivability.

Several different types of microorganisms have been identified as beneficial probiotics that improve the health of the host, including *Lactobacillus, Bifidobacterium, Enterococcus, Bacillus*, and yeasts. Probiotics tend to provide benefit to the host through three modes of action: 1) immunomodulation of the host's immune system; 2) shifts in the gastrointestinal microbial ecology through both direct and indirect effects on other microorganisms; 3) effect on bacterial metabolites, either toxins produced by pathogenic organisms or compounds that provide a nutrient advantage to beneficial organisms or the host (Soccol et al., 2010). *Bacillus* and yeasts are probiotic supplements used in livestock feed, as they tend to be stable and maintain viability in the relatively harsh conditions of feed mixing and storage, compared to *LactoBacillus* or *Bifidobacterium* organisms. Consequently, there are examples in the scientific literature of the beneficial effects of administering either yeasts or *Bacillus* on health and production of swine herds.

Formulated yeast has been shown to improve birth weights, improve piglet survivability (reduced mortality) and increase the number and weight of pigs weaned (Bass et al., 2012). Research has shown that formulating the components of yeast to specific levels of beta-glucan, mannan oligosaccharide, nucleotide content, and yeast metabolites can increase the animal performance response when yeast is included in the diets as well as the predictability of the response (Lindemann et al., 2010). The beta-glucan component of yeast activates and potentiates the immune response, improving the protection from pathogenic bacteria in pigs (Vetvicka et al., 2014), Additionally, beta-glucan has the ability to bind certain mycotoxins as well as improve liver function. Beta 1,3 and beta 1,6 glucans have been shown to improve immune response, whereas beta 1,4 glucan does not improve the immune response (Galliano et al, 2012; Jang et al., 2013). Dried yeast has been shown to be an immune system stimulant that promotes the growth of beneficial bacteria, while inhibiting pathogenic bacteria. (Jurgens et al., 1997). Feeding dried yeast to the sow improved milk IgG, and did not impact lactation performance, however improved subsequent performance post-weaning. Pigs fed mannan-oligosacchrides post-weaning had improved growth performance compared to control fed pigs (Miguel et al., 2004). The effect is even more pronounced in pigs from a lower health status.

Providing nucleotides derived from yeast to the young pig has been linked to increasing feed intake and improving the transition from mother's milk to solid feed (Plante et al., 2011). Milk tends to be high in nucleotides, whereas typical feed ingredients are relatively low. By supplementing yeast nucleotides, intestinal growth and maturation is enhanced during a high period of stress caused by weaning the pig from the sow (Plante et al., 2011). The yeast metabolites also contain glutamic acid which supports feed intake. The young pig is limited in feed intake capacity, thus stimulating feed intake is a priority in weaned pigs to assure a positive transition from a milk diet to solid feed.

Yeast culture has been fed to gestating/lactating sows in an attempt to improve pre-weaning mortality and improve litter weight gain (Kim et al., 2010; Veum et al., 1995). In both studies, feeding a yeast culture did not improve the performance of pigs during lactation, nor did it improve sow feed utilization. In contrast, feeding a dried yeast has been shown to improve post-weaning performance, but did not impact litter performance prior to weaning (Jurgens et al., 1997). By formulating yeast to specific components and fed to sows during gestation and lactation, piglet birth weight and weaning weight were increased compared to control fed sows (Lindemann et al., 2010). Post-weaning performance was also impacted by feeding sows a formulated yeast product during gestation and lactation. Weaning weight was heavier in pigs from yeast fed sows compared to control fed sows, resulting in a greater average daily gain. (ADG) and final weights. When the data was adjusted for initial weight, the pigs from sows fed yeast had improved feed conversion as well.

*Bacillus* probiotics have been reported to increase body weight gain and improve efficiency of feed utilization when administered to pigs (Chen et al., 2006; Davis et al, 2008; Hong et al., 2005). The growth promoting effects of *Bacillus* probiotics fed to pigs have been attributed its ability to produce antimicrobial compounds and inhibit the growth of enteric pathogens (Hentges et al., 1992). Consequently, through the production of antimicrobial compounds and the inhibition of some enteric microbial species, *Bacillus* probiotics shift the microbial population in the gastrointestinal tract, making the enteric environment less hospitable to pathogenic organisms and enhancing beneficial populations of *Lactobacillus* (Cui, et al., 2013; Baker et al., 2013). Furthermore, beneficial effects have been observed in piglets when sows were administered a *Bacillus* probiotic, including increases in weaning weight, less diarrheal scours, and reduction in *E. coli* and *Clostridium* levels in the gastrointestinal tract (Baker et al., 2013; Maruta et al., 1996). These effects from *Bacillus* probiotics are similar to the benefits from the administration of growth promoting antibiotics, and *Bacillus* have been reported to improve growth performance in pigs similarly to antibiotic supplemented feed (Hu et al., 2014). Some examples exist in the literature that report on the effects of feeding a combination of yeast-based products with *Bacillus* probiotics to livestock and poultry. An enzymatically hydrolyzed yeast product and a *Bacillus*

*subtilis* probiotic were fed singly and in combination to broiler chickens, and the study concluded that no synergistic relationship was observed in response to this specific yeast-*Bacillus* combination, although the effects of the combination could be considered additive (Gomez et al., 2012). A study evaluating a combination of live *Saccharomyces* and *Bacillus* strains fed to growing-finishing pigs found there was no benefit in the yeast/*Bacillus* combination over feeding the *Bacillus* strain alone (Giang et al., 2011). A combination of live yeasts, i.e., *Saccharomyces cerevisiae*, fungus, i.e., *Aspergillus oryzae*, and bacteria strains (*Lactobacillus acidophilus* and *Bacillus subtilis*) fed to weaned pigs improved growth performance over pigs fed an untreated control diet, but effects of the individual components of the combination were not evaluated (Choi et al., 2011). Another study evaluating the combination of a *Bacillus* probiotic with an active dried yeast product did not report any additional improvement in growth performance when fed to weaned pigs over that observed when feeding the individual components (Barker et al., 2003). Furthermore, an active yeast combined with a *Bacillus subtilis* and *Bacillus licheniformis* combination probiotic did not improve growth performance or nutrient digestibility over the yeast or *Bacillus* combination alone when fed to weaned pigs (Min et al., 2003), These data suggest that combining some yeast products (whether a live or nonviable strain) with a *Bacillus*-based probiotic affords no additional benefit when fed to pigs compared to the benefits observed from feeding each singly.

Antibiotic growth promotors are used extensively to control health challenges, enhance lean tissue gain, and improve efficiency of feed utilization in swine production. But use of antibiotic technologies will soon become less prevalent as the Veterinary Feed Directive is implemented in 2017, restricting and aggressively regulating the use of antibiotic use in livestock and poultry diets. Swine producers desire effective alternatives to antibiotics that will provide a similar benefit to their production efficiency as sub-therapeutic antibiotic use. The effects of yeasts and *Bacillus* probiotics outlined in this paper offer some of the same benefits as growth promoting antibiotics, although often to lesser degree and with less consistency. The swine industry is in need of alternative technologies to manage their herd health and production efficiency through all swine growth production stages in the absence of sub-therapeutic antibiotic use. Optimally, this antibiotic alternative would be easy to implement on-farm and provide multiple benefits to herd health and pork production from birth to market.

SUMMARY OF THE INVENTION

The present invention, is intended to solve one or more of the problems noted above. In accordance with an embodiment of the present invention, the disclosure relates to a composition comprising a biologically pure culture of one or more *Bacillus* strains selected from the group consisting of: *Bacillus subtilis* 1104 and *Bacillus subtilis* 2084; and a formulated yeast product. (Accession Numbers: ABS1104 NRRL B-67258 and BS2084 NRRL B-50013). As used herein, the formulated yeast product may comprise a combination of *Saccharomyces cerevisiae* yeast extract representing approximately 25-80% of the total formulated yeast product by weight, hydrolyzed yeast representing approximately 5-40% of the total formulated yeast product by weight, a yeast culture representing approximately 5-50% of the total formulated yeast product by weight. The formulated yeast may also comprise limestone representing approximately 5-50% of the total formulated yeast product by weight.

In one embodiment, the disclosure relates to a composition having a biologically pure culture of one or more *Bacillus* strains selected from the group consisting of: *Bacillus subtilis* 1104 and *Bacillus subtilis* 2084.

In one embodiment, the disclosure relates to a composition having an isolated biologically pure culture of one or more *Bacillus* strains selected from the group consisting of: *Bacillus subtilis* 1104 and *Bacillus subtilis* 2084.

In one embodiment, the disclosure relates to a composition of *Saccharomyces cerevisiae* yeast product having one or more of a *Saccharomyces cerevisiae* yeast extract, a hydrolyzed *Saccharomyces cerevisiae* yeast, and a *Saccharomyces cerevisiae* myeast culture, In one embodiment, the disclosure relates to a composition having a biologically pure culture of one or more *Bacillus* strains selected from the group consisting of: *Bacillus subtilis* 1104 and *Bacillus subtilis* 2084; a *Saccharomyces cerevisiae* yeast product.

In one embodiment, the *Saccharomyces cerevisiae* yeast product may include one or more of a *Saccharomyces cerevisiae* yeast extract, a hydrolyzed *Saccharomyces cerevisiae* yeast, and a *Saccharomyces cerevisiae* yeast culture.

In one embodiment, the *Saccharomyces cerevisiae* yeast product may contain between 25 and 80 percent by weight of the *Saccharomyces cerevisiae* yeast extract, between 5 and 40 percent by weight of the hydrolyzed *Saccharomyces cerevisiae* yeast, and between 5 and 50 percent by weight of the *Saccharomyces cerevisiae* yeast culture.

In one embodiment, the compositing may comprise at least in part a direct fed microbial. In one embodiment, the compositing may also include a carrier selected from at least one of whey, maltodextrin, sucrose, dextrose, limestone, rice hulls, and sodium silica aluminate.

In one embodiment, the compositing may also include a preservative.

In one embodiment, the compositing may also include an animal feed.

In one embodiment, the compositing may also include a volume of feedstuff.

In one embodiment, the composition in an animal feed has a concentration of the biologically pure culture of one or more *Bacillus* strains in the composition of about between 1×10e4 and 1×10e9 CFU/g of feed.

In one embodiment, the composition in an animal feed is consumed by an animal and has resultant concentration of the biologically pure culture of one or more *Bacillus* strains introduced into the animal in the range of about between 1×10e5 and 1×10e11 CFU/animal/day.

In one embodiment, the disclosure is related to composition having a biologically pure culture of one or more *Bacillus* strains selected from the group consisting of: *Bacillus subtilis* 1104 and *Bacillus subtilis* 2084 for use in increasing the performance of a swine.

In one embodiment, the disclosure is related to composition having a biologically pure culture of one or more *Bacillus* strains selected from the group consisting of: *Bacillus subtilis* 1104 and *Bacillus subtilis* 2084 for use in increasing the performance of a swine.

In one embodiment, the disclosure relates to a method of improving immune system function of an animal comprising administering to the animal an effective amount of the composition described herein.

In one embodiment, the method of improving immune system function is a method of improving immune system function in a swine having been administered an effective amount of the composition described herein.

In one embodiment, the method of improving immune system function is a method of improving immune system function in an offspring of a sow having been administered an effective amount of the composition described herein.

In one embodiment, the disclosure relates to a method of improving immune system function of an offspring of an animal comprising administering to the animal an effective amount of the composition described herein.

In one embodiment, the disclosure relates to a method of reducing inflammation in an animal comprising administering to an animal an effective amount of the composition described herein.

In one embodiment, the disclosure relates to a method of reducing inflammation in an offspring of an animal comprising administering to the animal an effective amount of the composition described herein.

In one embodiment, the disclosure relates to a method of improving survivability in a group of animals comprising administering to the group of animal an effective amount of the composition described herein.

In one embodiment, the disclosure relates to a method of improving survivability in a group of offspring of a group of animals comprising administering to the group of animals an effective amount of the composition described herein.

In one embodiment, the disclosure relates to a method of decreasing mortality in a group of animal comprising administering to the group of animal an effective amount of the composition described herein.

In one embodiment, the disclosure relates to a method of decreasing mortality in a group of offspring to a group of animals comprising administering to the group of animals an effective amount of the composition described herein.

In one embodiment, the disclosure relates to a method of increasing interferon gamma in an animal comprising administering to an animal an effective amount of the composition described herein.

In one embodiment, the disclosure relates to a method of increasing interferon gamma in an offspring of an animal comprising administering to the animal an effective amount of the composition described herein.

In one embodiment, the disclosure relates to a method of increasing pigs' weight born to a sow comprising administering to the sow an effective amount of the composition described herein.

In one embodiment, the disclosure relates to a method of providing reduced pathogenic bacteria counts in a gut of an animal comprising administering to the animal an effective amount of the composition described herein.

In one embodiment, the disclosure relates to a method of providing reduced pathogenic bacteria counts in a gut of an offspring of an animal comprising administering to the animal an effective amount of the composition described herein.

BRIE DESCRIPTION OF THE DRAWING

FIG. 1. A graph displaying principal component analysis of fecal microbial ecology data comparing gestating sows fed a 1) Control, basal diet; 2) Bacillus subtilis two-strain direct-fed microbial (DFM; Bacillus subtilis ABS1104 NRRL B-67258; Bacillus subtilis BS2084 NRRL B-50013); 3) formulated yeast containing yeast extract, hydrolyzed yeast, and yeast culture(Yeast); or 4) Bacillus combination+formulated yeast (Y+DFM).

Figure 2:
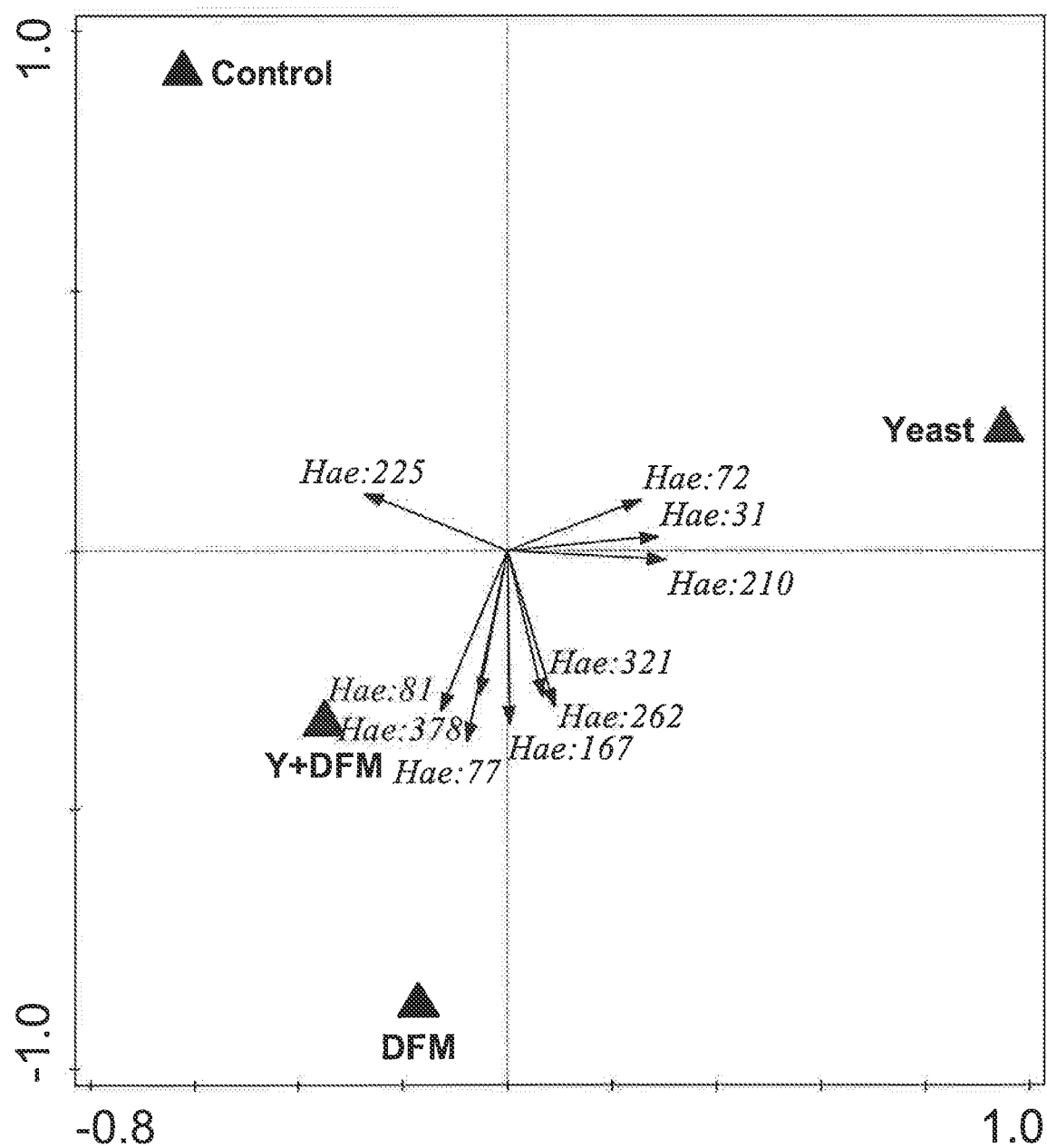

FIG. 2. A graph displaying principal component analysis of fecal microbial ecology data comparing lactating sows fed a 1) Control, basal diet; 2) Bacillus subtilis two-strain combination (ABS1104 NRRL B-67258; BS2084 NRRL B-50013); 3) formulated yeast containing yeast extract, hydrolyzed yeast, and yeast culture (Yeast); or 4) Bacillus combination+formulated yeast (Y+DFM).

Figure 3:
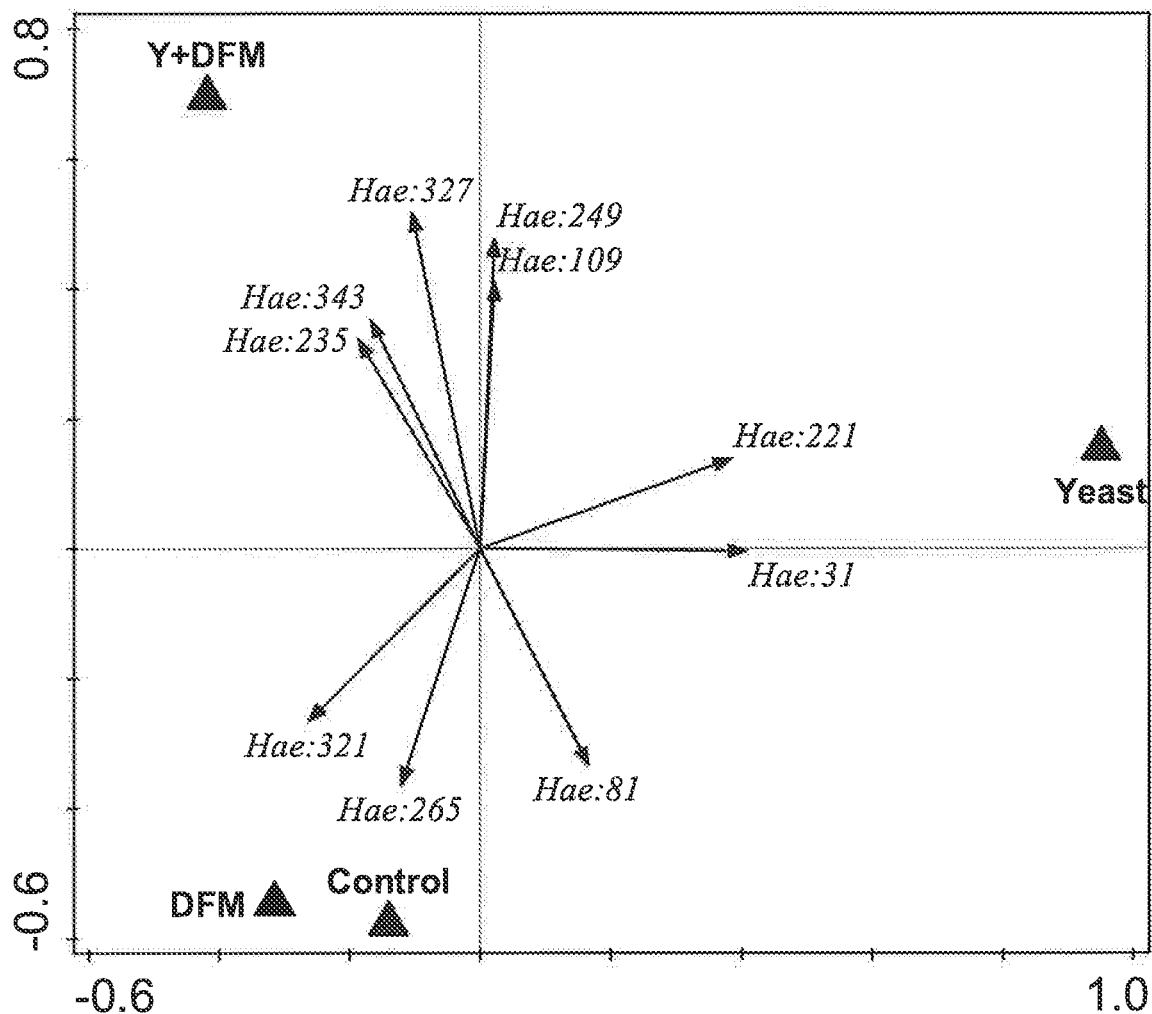

FIG. 3. A graph displaying principal component analysis of fecal microbial ecology data comparing 5 day old piglets from sows fed a 1) Control, basal diet; 2) Bacillus subtilis two-strain direct-fed microbial (DFM; Bacillus subtilis ABS1104 NRRL B-67258; Bacillus subtilis BS2084 NRRL B-50013); 3) formulated yeast containing yeast extract, hydrolyzed yeast, and yeast culture (Yeast); or 4) Bacillus combination+formulated yeast (Y±DFM).

Figure 4:
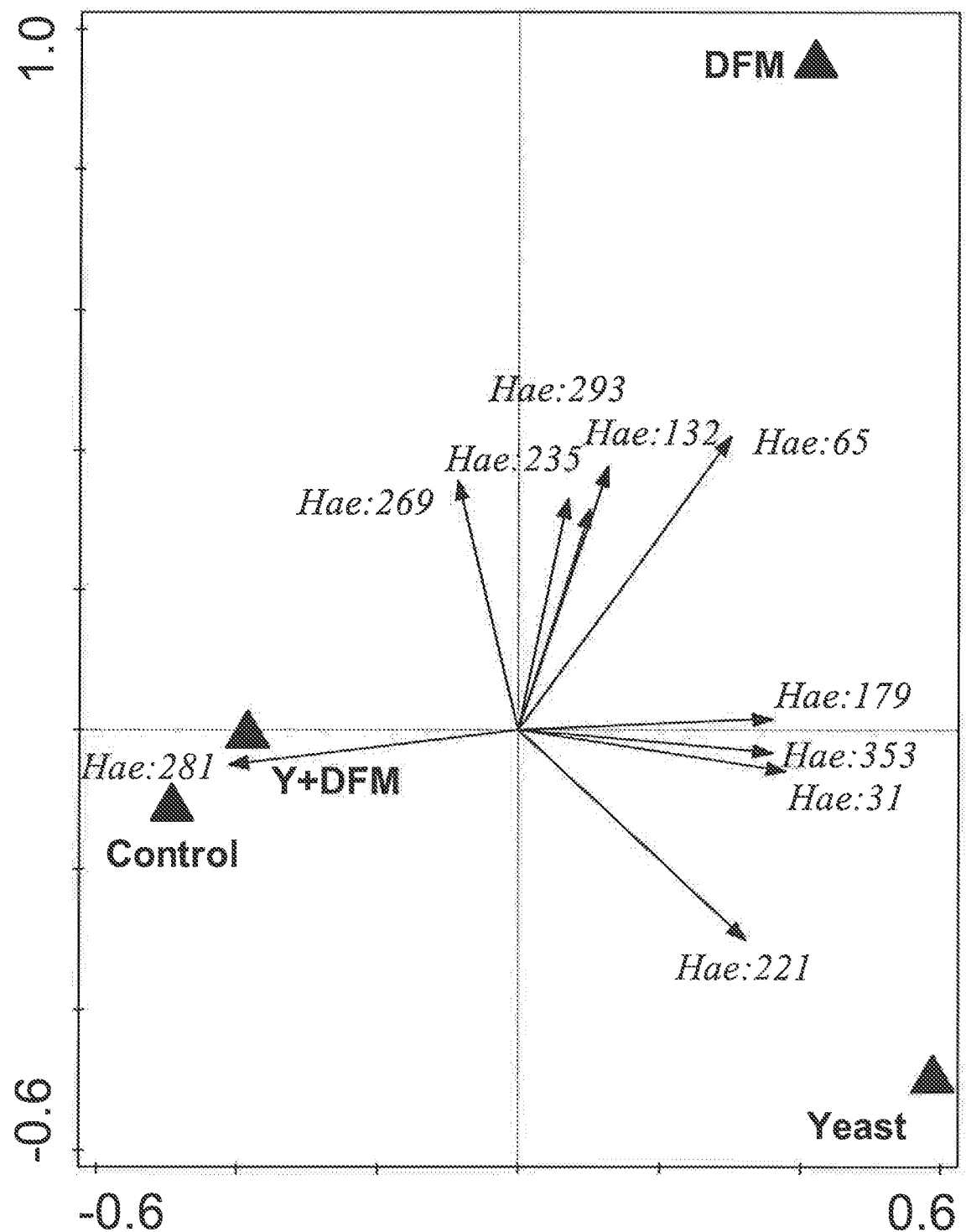

FIG. 4. A graph displaying principal component analysis of fecal microbial ecology data comparing 18 day old piglets from sows fed a 1) Control, basal diet; 2) Bacillus subtilis two-strain direct-fed microbial (DFM; Bacillus subtilis ABS1104 NRRL B-67258; Bacillus subtilis BS2084 NRRL B-50013); 3) formulated yeast containing yeast extract, hydrolyzed yeast, and yeast culture (Yeast); or 4) Bacillus combination+formulated yeast (Y+DFM).

Figure 5:
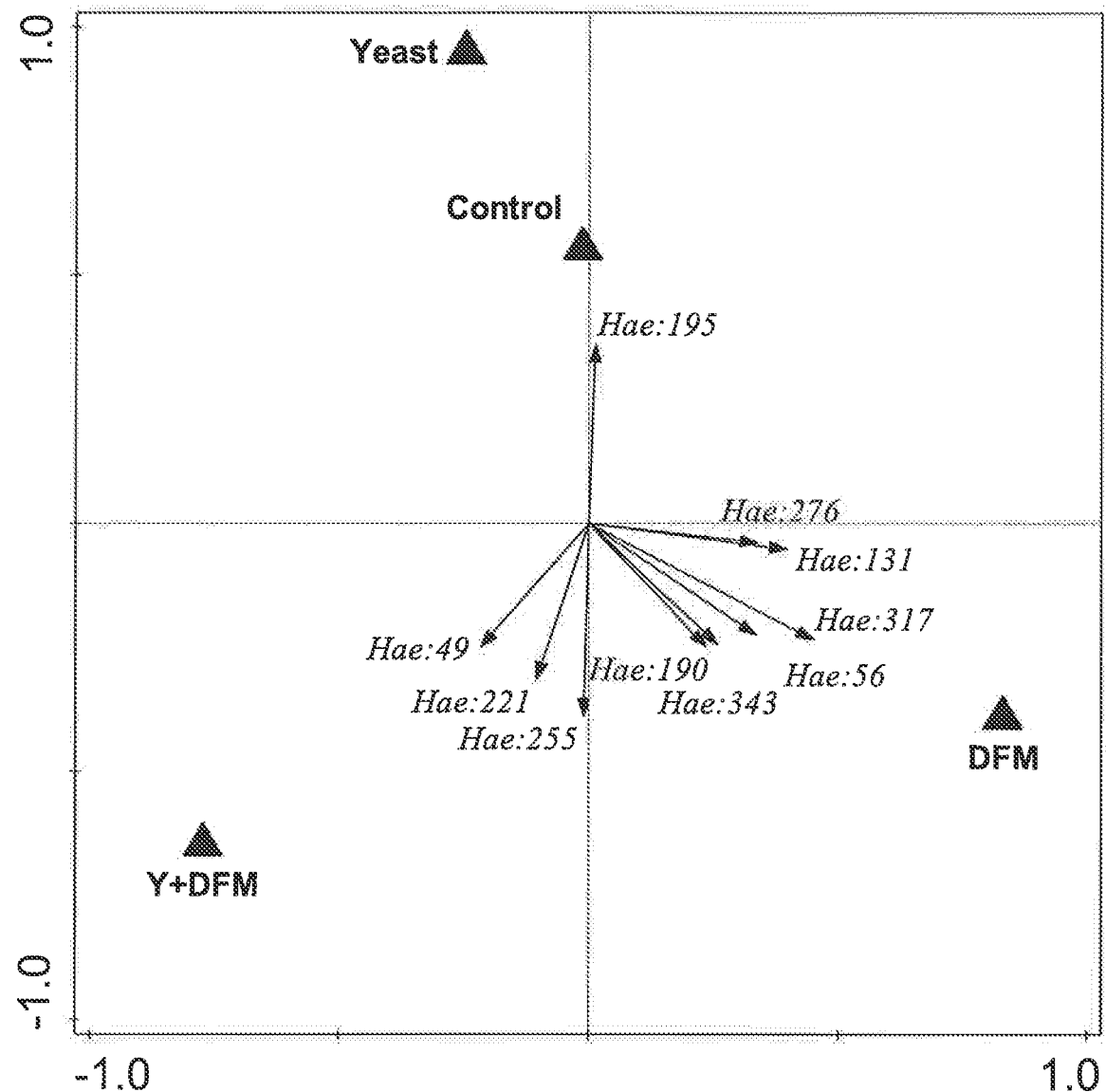

FIG. 5. A graph displaying principal component analysis of fecal microbial ecology data comparing 24-day old weaned nursery pigs born to sows fed a 1) Control, basal diet; 2) Bacillus subtilis two-strain direct-fed microbial (DFM; Bacillus subtilis ABS1104 NRRL B-67258; Bacillus subtilis BS2084 NRRL B-50013); 3) formulated yeast containing yeast extract, hydrolyzed yeast, and yeast culture (Yeast); or 4) Bacillus combination+formulated yeast (Y+DFM).

Figure 6:
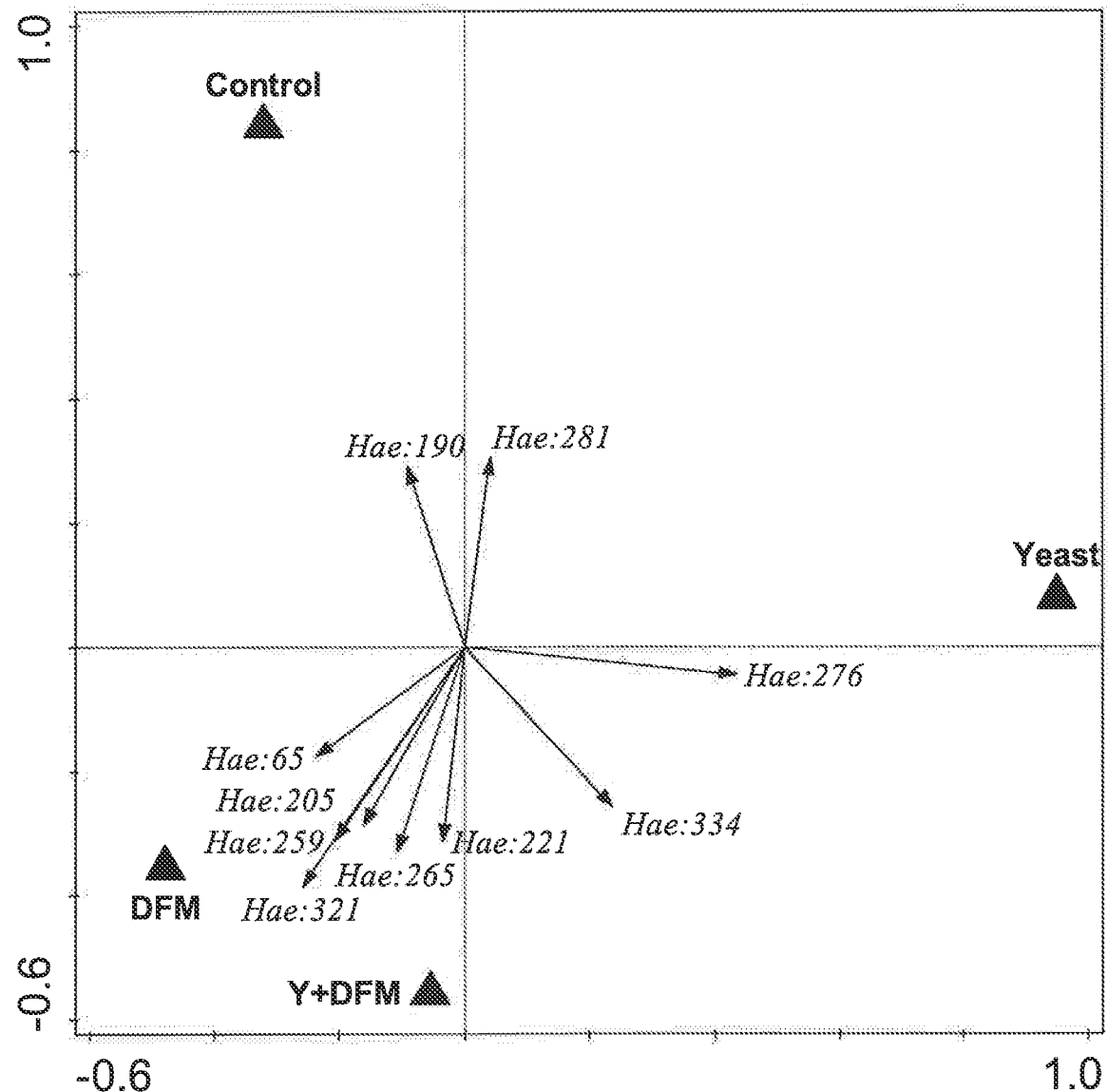

FIG. 6. A graph displaying principal component analysis of fecal microbial ecology data comparing 35-day old weaned nursery pigs born to sows fed a 1) Control, basal diet; 2) Bacillus subtilis two-strain direct-fed microbial (DFM; Bacillus subtilis ABS1104 NRRL B-67258; Bacillus subtilis BS2084 NRRL B-50013); 3) formulated yeast containing yeast extract, hydrolyzed yeast, and yeast culture (Yeast); or 4) Bacillus combination±formulated yeast (Y+DFM).

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

Unless defined otherwise, all technical and scientific terms used herein have the same meaning as commonly understood by one of ordinary skill in the art to which this disclosure belongs. Singleton, et al, DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure, which can be had by reference to the specification as a whole. Accordingly, the terms defined immediately below are more fully defined by reference to the specification as a whole.

It is noted that, as used in the specification and the appended claims, the singular forms "a," "an," and "the" include plural referents unless the context clearly dictates otherwise. The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, melt index, temperature etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to he 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to he considered to be expressly stated in this disclosure. Numerical ranges are provided within this disclosure for, among other things, relative amounts of components in a mixture, and various temperature and other parameter ranges recited in the methods.

As used herein, "administer" is meant the action of introducing the strain, the formulated yeast, and/or the combination thereof to an environment.

As used herein, the term "animal" includes but is not limited to human, mammal, amphibian, bird, reptile, pigs, cows, cattle, goats, horses, sheep, poultry, and other animals kept or raised on a farm or ranch, sheep, big-horn sheep, buffalo, antelope, oxen, donkey, mule, deer, elk, caribou, water buffalo, camel, llama, alpaca, rabbit, mouse, rat, guinea pig, hamster, ferret, dog, cat, and other pets, primate, monkey, ape, and gorilla. In some embodiments, the animals are pig, including but not limited to sows, piglets and grow-finish.

By "at least one strain," is meant a single strain but also mixtures of strains comprising at least two strains of bacteria. By "a mixture of at least two strains," is meant a mixture of two, three, four, five, six or even more strains. In some embodiments of a mixture of strains, the proportions can vary from 1% to 99%. In certain embodiments, the proportion of a strain used in the mixture is at least 5%, 10%, 15%, 20%, 25%, 30%, 35%, 40%, 45%, 50%, 55%, 60%, 65%, 70%, 75%, 80%, 85%, 90%, or 95%. Other embodiments of a mixture of strains are from 25% to 75%. Additional embodiments of a mixture of strains are approximately 50% for each strain. When a mixture comprises more than two strains, the strains can be present in substantially equal proportions in the mixture or in different proportions.

As used herein, the term "feed" refers to a commercial feed. Feeds may he blended from various raw materials and additives. These blends are formulated according to the specific requirements of the target animal.

As used herein, "effective amount" is meant a quantity of strain, formulated yeast and/or the combination thereof to improve performance of an animal. Improvement in performance can be measured as described herein or by other methods known in the art. An effective amount can be administered to the animal by providing ad libitum access to feed containing the strain, the formulated yeast and/or the combination thereof. The strain, the formulated yeast and/or the combination thereof can also he administered in one or more doses.

As used herein, the term "feed" is used synonymously herein with "feedstuff."

As used herein, the term "feed component" refers to all or part of the feedstuff Part of the feedstuff may mean one constituent of the feedstuff or more than one constituent of the feedstuff e.g. 2 or 3 or 4. The term "feed component" encompasses a premix or premix constituents.

As used herein, "performance" refers to the productivity of an animal, such as a pig or poultry, measured by one or more of the following parameters: scours, mortality, number of pigs born, born alive, litter birth weight, survivability, immune system function, inflammation. "An improvement in performance" or "improved performance" as used herein, refers to an improvement in at least one of the parameters listed under the performance definition.

As used herein, the term "protein" includes proteins, polypeptides, and peptides.

In one embodiment, the disclosure relates to one or more bacterial strains. In yet another embodiment, the disclosure relates to a composition comprising one or more bacterial strains. The bacterial strains may be selected from *Bacillus subtilis* 1104 and *Bacillus subtilis* 2084 (deposits were made under the Budapest Treaty and assigned Accession Numbers, ABS1104 NRRL B-67258 and BS2084 NRRL B-50013, respectively). In yet another embodiment, the disclosure relates to a composition comprising a formulated yeast. The formulated yeast may comprise a combination of *Saccharomyces cerevisiae* yeast extract representing approximately 25-80% of the total formulated yeast by weight, hydrolyzed yeast representing approximately 5-40% of the total formulated yeast by weight, a yeast culture representing approximately 5-50% of the total formulated yeast by weight. The formulated yeast may also comprise limestone representing approximately 5-50% of the total formulated yeast product by weight. The composition may be a liquid, a mixture, a solid, a powder, a solution, a dispersion, lyophilized, freeze-dried, or any combination thereof.

In one embodiment, the composition is a feed additive. In one embodiment, concentrations of the composition may be adjusted as described herein for administration to the desired animal stage. In one embodiment, the animal is a pig.

In one embodiment, one or more carriers or other ingredients can be added to the composition as disclosed herein. The composition may be administered in various physical forms, for example, a top dress, a water soluble concentrate, gels or gelatin capsules. Additives may include, but are not limited to growth substrates, enzymes, sugars, carbohydrates, extracts, and growth promoting ingredients.

The *Bacillus* strains can be produced by fermentation of the bacterial strains by growing in a liquid nutrient broth. In at least one embodiment, the *Bacillus* strains are grown to a level at which the highest number of spores are formed. In a non-limiting example, fermentation can be started by scaling-up a seed culture. This involves repeatedly and aseptically transferring the culture to a larger and larger volume to serve as the inoculum for the fermentation, which is carried out in large stainless steel fermenters in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

In one embodiment, to prepare the *Bacillus* strains, each *Bacillus* strain is fermented to a $5 \times 10^3$ CFU/ml to about $4 \times 10^{12}$ CFU/ml level. The bacteria are harvested by centrifugation, and the supernatant is removed. In some embodiments, the bacteria is pelleted bacteria. In at least some embodiments, the pelleted bacteria are freeze-dried and mixed with a carrier. The strains can also be used with or without preservatives, and in concentrate, unconcentrated, or diluted form.

The count of the culture can then be determined. CFU or colony forming unit is the viable cell count of a sample resulting from standard microbiological plating methods.

The term is derived from the fact that a single cell when plated on appropriate medium will grow and become a viable colony in the agar medium. Since multiple cells may give rise to one visible colony, the term colony forming unit is a more useful unit measurement than cell number.

In another embodiment, the disclosure relates to a feed additive composition that may be used as a feed or in the preparation of a feed. The feed may be in the form of a solution or as a solid depending on the use and/or the mode of application and/or the mode of administration. When used as a feed or in the preparation of a feed, such as functional feed, the feed additive composition may be used in conjunction with one or more of the following: a nutritionally acceptable carrier, a nutritionally acceptable diluent, a nutritionally acceptable excipient, a nutritionally acceptable adjuvant, a nutritionally active ingredient. In one embodiment, the feed additive composition disclosed herein is mixed with a feed component to form a feedstuff. In one embodiment, the feed may be a compound feed, or a premix thereof. In one embodiment, the feed additive composition disclosed herein may be admixed with a compound feed, a compound feed component or a premix of a compound feed.

Compound feeds can be complete feeds that provide all the daily required nutrients, concentrates that provide a part of the ration (protein, energy) or supplements that only provide additional micronutrients, such as minerals and vitamins. The main ingredients used in compound feed are the feed grains, which include corn, soybeans, sorghum, oats, and barley. A premix, as referred to herein, may be a composition composed of micro-ingredients such as vitamins, minerals, chemical preservatives, antibiotics, fermentation products, and other essential ingredients. Premixes are usually compositions suitable for blending into commercial rations.

In one embodiment, a feedstuff as disclosed herein may comprise one or more feed materials selected from the group comprising cereals, such as small grains (e.g., wheat, barley, rye, oats and combinations thereof) and/or large grains such as maize or sorghum; byproducts from cereals, such as corn gluten meal, distillers grains, wheat bran, wheat middlings, wheat shorts, rice bran, rice hulls, oat hulls, palm kernel, and citrus pulp; protein obtained from sources such as soya, sunflower, peanut, lupin, peas, fava beans, cotton, canola, fish meal, dried plasma protein, meat and bone meal, potato protein, whey, copra, sesame; oils and fats obtained from vegetable and animal sources; and minerals and vitamins.

In yet another embodiment, a feedstuff may comprise at least one high fiber feed material and/or at least one by-product of the at least one high fiber feed material to provide a high fiber feedstuff. Examples of high fiber feed materials include: wheat, barley, rye, oats, by-products from cereals, such as corn gluten meal, distillers grains, wheat bran, wheat middlings, wheat shorts, rice bran, rice hulls, oat hulls, palm kernel, and citrus pulp. Some protein sources may also be regarded as high fiber: protein obtained from sources such as sunflower, lupin, fava beans and cotton.

In still another embodiment, the feed may be one or more of the following: a compound feed and premix, including pellets, a crop or crop residue: corn, soybeans, sorghum, oats, barley, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

In one embodiment the composition as disclosed herein is mixed with the feedstuff.

Alternatively, the composition may be included in the emulsion or raw ingredients of a feedstuff.

In one embodiment, the disclosure relates to methods of increasing performance metrics of an animal. In another embodiment, the disclosure relates to methods of increasing performance metrics of a pig as described above.

Administration of the composition according to this disclosure is possible at any time, with or without feed. However, as described herein, one preferred administration is with feed.

Thus, in at least some embodiments, the effective amount of the composition according to the present disclosure is administered in an animal by supplementing a feed intended for the animal. As used herein, "supplementing," refers to the incorporation of an effective amount of the composition provided herein into the feed for the animal. As such, the animal will ingest the composition provided herein during feeding.

EXAMPLES

The following Examples are provided for illustrative purpose only. The Examples are included herein solely to aid in a more complete understanding of the presently described invention. The Examples do not limit the scope of the invention described or claimed herein in any fashion.

Example 1

Yeast and *Bacillus* Combination Administered to Sows Improves Performance, Decreases Pathogen Load, and Modulates Immune Response in Sows and Their Offspring Objectives Sows were fed a formulated yeast and *Bacillus* combination product during the entire gestation and lactation periods to determine the impact on reproductive performance. Subsequent performance was measured in their offspring to determine if the feed treatments during the gestation and lactation had any impact on pig performance and survivability.

Animals and Experimental Diets

A total of 500 sows were identified for this study at 3 days post mating. On the first day of the experiment, each subgroup was randomly assigned to one of four treatment groups and blocked based on parity. Treatments included 1) a control, basal diet; 2) *Bacillus subtilis* two-strain combination (A 3S1104 NRRL B-67258; BS2084 NRRL B-50013); 3) yeast combination formulated to contain yeast extract, hydrolyzed yeast, and yeast culture; or 4) *Bacillus* combination+formulated yeast. Treatments 2, 3, and 4 were applied as a top dress to the Control basal diet (Table 1). After weaning a total of 1,100 mixed-sex weanling pigs from the sows fed control, *Bacillus subtilis* two-strain combination, formulated yeast, or *Bacillus* combination+formulated yeast diets were fed standard diets to determine if the treatments fed to the sow had impact on performance of the offspring post-weaning.

Experimental Design, Procedures, and Data Collection (Sow)

Animal Housing

Sows were fed twice per day based on their respective body condition score via a feed/water trough throughout the gestation period. Water was available on an ad libitum basis. On approximately d 112 of gestation, sows were moved to the farrowing barn and placed randomly in maternity pens. Diets were changed from gestation to lactation diets and were fed ad libitum for the entire lactation period.

Experimental Diets

Basal diets were standard gestation and lactation diets (Table 2). Formulated yeast and *Bacillus* was delivered to sows by top-dressing. During the gestation period, top-dressing was performed daily by dropping yeast, *Bacillus*, or both into feed troughs with the ration at prescribed rate when feeding in the morning. Care was taken assure water was not provided until the last sow finished eating her ration.

After farrowing and throughout the entire lactation period, top-dressing of yeast, *Bacillus*, or both at the rate prescribed for lactation was performed daily until weaning. On the day of weaning, sows were monitored to determine the weaning to rebreeding interval.

Data Collection

Individual sow body weight was measured (1) on the day sows were transferred to the farrowing barn, and (2) at weaning. The data were used to calculate the body weight loss during the lactation period using the formula: Sow 13W Loss=Wean—(PRE (LW+LW/5.5)), where Wean=sow weight at weaning; PRE=sow pre-farrow weight; LW=litter weight; LW/5.5=estimated placental weight (Fahmy and Bernard, 1971). Days of lactation and days from weaning to estrus was recorded. The number of piglets born (alive and dead), individual birth weight (alive and dead), individual weaning weight, and the number of piglets dead during lactation period were recorded for each litter. Cross-fostering and removal of unthrifty pigs was allowed within 24 hours after birth and only within treatments or to non-test litters.

Twenty-five sampling sows were selected from each treatment, and fecal samples were collected at the end of gestation (day 112-114) before entering the farrowing house and at the end of lactation (day 17-19) for the measurement and counts of *E. coli* and *Clostridium*.

Sow blood samples were collected from the same sampling sows at the end of gestation and lactation for the analyses of blood urea nitrogen. (BUN), non-esterified fatty acids (NEFAs), and glucose. From each sampling sow litter, fecal samples were collected from days 3 to 7 of age and from days 16 to 20 (at weaning) for the same microbial counts in piglets. Piglet blood samples were collected from 2 pigs per litter (one gilt and one barrow) from day 2 to 4 of age and at weaning for the same analyses as sows. Serum was collected from a subset of blood samples obtained from each sow and piglet for immunological measurements including the alpha-1-acid glycoprotein, interferon-gamma, and tumor necrosis factor-alpha.

Experimental Design & Procedures (Nursery)

Animal Housing

A total of 1,100 mixed-sex weanling pigs, which represented 22.8% of the total piglets weaned from the sow phase, were transferred to the Nursery Research Center for evaluation of post-weaning performance. Pigs with the same color of ear tags were grouped and randomly placed in 44 pens with 19-27 pigs per pen at arrival (d 0), The number of barrows and gilts were balanced within each pen. Off-test pigs (fallbacks and/or pigs without ear tag) were removed to non-test room.

Dietary Treatments

On day 0, pigs were weighed by pen. Pens were ranked and blocked by sow diet, initial BW and allotment date. All pens received a common diet for all phases for the evaluation of post-weaning survivability. This resulted in one basal diet for the nursery phases and a total of four treatments from the sow phase (Table 3).

Experimental Procedure

The nursery phase was conducted for 51 days in a 4-phase feeding program (Table 4) immediately after weaning. Feed was provided through the FeedLogic® system allowing collection of feed intake data by pen. Composition of the basal diets fed during each phase of the nursery period are shown in Table 5.

Data Collection

Fecal samples were collected at two time points from each pen for microbial counts on day 3 and 14 post-weaning. Two barrows were selected from each pen and tagged for future sampling, and blood was collected on day 0, at the end of Phase 2, and at the end of Phase 4 with individual weights at each time point for immunological analyses.

Statistical Analysis

Data were analyzed using ANOVA by the MIXED procedure of SAS. For sow phase, sow/litter served as the experimental unit. The statistical model included fixed effect of dietary treatments and a covariate of parity. For nursery phase, the pen served as the experimental unit. The statistical model included fixed effect of sow treatments and random effect of block. Initial pen body weight ("BW") was used as covariate for analysis of parameters for nursery phase. Multiple comparisons between treatments were performed using the Tukey adjustment option of SAS. All results were reported as least squares means. The significance level chosen was α=0.05. Treatment effect was considered significant if P<0.05, whereas values between 0.05≤P≤0.10 were considered as statistical trends.

Results:

Sow litter performance (total number born, total born alive, litter birth weight, etc.) was not affected by treatments administered to sows (Table 6). Piglet weaning weight was only slightly altered when the formulated yeast product or *Bacillus* treatments were fed singly, but a 1% increase was observed when the formulated yeast product and *Bacillus* treatments were fed to sows in combination. A slight decrease in *E. coli* counts in sow fecal samples was observed both before farrowing and at weaning for sows fed the *Bacillus* treatment (−1.3% and −1.9%, respectively), whereas a slight increase in fecal *E. coli* counts was observed during the same time periods when the formulated yeast product was fed to sows (+1.5% and +1.2%, respectively); Table 7). However, when the *Bacillus* treatment and formulated yeast products were administered to sows in combination, a much greater reduction in sow fecal *E. coli* counts was observed both before farrowing and at weaning (−6.4% and −7.2%, respectively; Table 7).

The acute phase protein, alpha-1-acid glycoprotein, was decreased slightly in the serum of sows at weaning when the Bacillus treatment or the formulated yeast product was fed singly to sows (−13.1% vs.−14.2% for DFM vs. formulated yeast product, respectively), however the acute phase protein was decreased substantially more when the Bacillus treatment and formulated yeast product were combined and administered to the sow (−48.0%; Table 8). Tumor necrosis factor-alpha was increased in the serum of piglets at weaning when the Bacillus treatment or the formulated yeast product were administered to their sows singly, but decreased (−6.8%) in the offspring at weaning of sows treated with both the Bacillus treatment and formulated yeast in combination (Table 8). A slight decrease was observed in piglets from sows administered either the Bacillus treatment or the formulated yeast product singly (−2.8% and −9.5%, respectively), however a substantially greater decrease was observed in piglets when the two feed additives were fed to sows in combination (−16.3%). At weaning, serum alpha-1-acid glycoprotein concentrations were increased in pigs from sows administered either the Bacillus treatment or the formulated yeast product singly, but was decreased in pigs from sows fed the two feed additives in combination (−6.8%). Taken together these data indicate that feeding the Bacillus treatment in combination with a formulated yeast product to sows substantially decreases the inflammation associated with production in sows and their piglets in early life compared to administering either to the sow singly.

Furthermore, pigs from sows fed the yeast treatment had reduced fecal E. coli concentrations 3 days post-weaning compared to pigs from unsupplemented sows, whereas pigs from sows fed the Bacillus treatment had increased populations of lactic acid bacteria (Table 10).

Administering the formulated yeast and the Bacillus combination to sows during gestation and lactation had the greatest effect on immunological competence of their offspring during the post-weaning nursery period. Relative to control pigs, interferon-δ (IFN-δ) was increased by 180.8% at weaning in pigs born to sows fed the yeast+Bacillus combination compared to 17.1% and 50.3% in pigs born to sows fed the Bacillus or yeast treatments, respectively (Table 11). Also at weaning, tumor necrosis factor-α (TNF-α) was increased relative to control pigs by 98.5% in pigs born to fed the yeast+Bacillus combination compared to only 67.2% in pigs born to sows fed the Bacillus and a reduction (−16.6%) in pigs from sows fed yeast. At the end of the Phase 2 nursery period, TNF-α was increased relative to control pigs by 254.3% in pigs born to sows fed the yeast+Bacillus combination compared to 61.6% and 56.0% in pigs born to sows fed the Bacillus or yeast treatments, respectively.

TABLE 1

Dietary treatments administered to sows during gestation and lactation phases.

| | Treatment | Additive | Inclusion Rate | Daily dose in gestation[1] | Daily dose in lactation[2] | No. of sows |
|---|---|---|---|---|---|---|
| 1. | Control | None | — | — | — | 125 |
| 2. | Yeast | Yeast[3] | 1.0 lb/ton | 1.13 gram/d | 2.26 gram/d | 125 |
| 3. | Bacillus | Bacillus[4] | 1.0 lb/ton | $8.5 \times 10^8$ CFU/d (10 g scoop/d) | $1.7 \times 10^9$ CFU/d (20 g scoop/d) | 125 |
| 4. | Bacillus + Yeast | Bacillus[4] + Yeast[3] | 1.0 lb/ton | Yeast: 1.13 g/d Bacillus: 10 g scoop/d | Yeast: 2.26 gram/d Bacillus: 10 g scoop/d | 125 |

[1]Dose was calculated based on the assumption that the average feed intake of sows in gestation is 5.0 lb/day.
[2]Dose was calculated based on the assumption that the average feed intake of sows in lactation is 12.0 lb/day.
[3]Yeast is formulated to contain yeast extract, hydrolyzed yeast, and yeast culture.
[4]Bacillus probiotic is comprised of 50% of Bacillus subtilis strain ABS1104 (NRRL B-67258) and 50% of Bacillus subtilis BS2084 (NRRL B-50013) targeting a total of $3.75 \times 10^5$ CFU per gram of feed

TABLE 2

Diet and nutrient composition for gestation and lactation basal diets on an as-fed basis

| Ingredient, lb | Gestation Diet | Lactation Diet |
|---|---|---|
| Corn | 1,523.15 | 1,262.95 |
| Soybean meal | 297.34 | 599.22 |
| Salt | 12.00 | 12.00 |
| Calcium Carbonate 38% | 26.48 | 15.61 |
| Dicalcium phosphate | 25.82 | 23.02 |
| Fat-Fancy Tallow | 2.50 | 71.40 |
| L-Lysine HCL 78.8% | 0.00 | 3.24 |
| DL Methionine-Dry 99% | — | — |
| Threonine | 0.00 | 0.71 |
| Tryptophan 100% | — | — |
| Phytase | 0.28 | 0.35 |
| Tribasic Copper Chloride | — | — |
| Vitamin/trace mineral Premix | 5.00 | 5.00 |
| Wheat middlings | 100.00 | 0.00 |
| Choline Chloride-60 | 0.93 | 0.00 |
| SALCURB | 6.50 | 6.50 |
| Total | 2000.00 | 2000.00 |
| Calculated nutrient composition | | |
| Crude Protein, % | 13.22 | 18.70 |
| Fat, % | 2.65 | 5.65 |
| SW NE net energy, kcal/kg | 2,250.00 | 2,400.00 |
| Lysine, % | 0.65 | 1.15 |
| Digestible lysine, % | 0.57 | 1.04 |
| Calcium, % | 0.81 | 0.61 |
| Phosphorus, % | 0.60 | 0.58 |
| Calcium/Phosphorus Ratio | 1.35 | 1.95 |

TABLE 3

Experimental treatments to evaluate carryover effects of sow treatments in the nursery.

| Treatment | Sow diet[1] | Nursery diet[2] | # of Pens | # of Pigs |
|---|---|---|---|---|
| A | Control | Control | 11 | 270 |
| B | Yeast | Control | 9 | 235 |
| C | Bacillus | Control | 13 | 308 |

TABLE 3-continued

Experimental treatments to evaluate carryover effects of sow treatments in the nursery.

| Treatment | Sow diet[1] | Nursery diet[2] | # of Pens | # of Pigs |
|---|---|---|---|---|
| D | Formulated Yeast/Bacillus | Control | 11 | 287 |

[1]Sow dietary treatments administered during gestation and lactation phases are described in detail in Table 2.
[2]Nursery basal diets for each phase are described in Table 5.

TABLE 4

Feeding program for nursery phases:

| Nursery Phase | Diet[1] | Days on Feed |
|---|---|---|
| Phase 1: 9-15 lb BW | Basal | 11 |
| Phase 2: 15-25 lb BW | Basal | 12 |
| Phase 3: 25-40 lb BW | Basal | 14 |
| Phase 4: 40-55 lb BW | Basal | 14 |

[1]Nursery basal diets for each phase are described in Table 5.

TABLE 5

Composition of basal diets fed to pigs in each nursery phase, on an as-fed basis.

| Ingredient, lb/ton | Basal diets | | | |
|---|---|---|---|---|
| | Phase 1 | Phase 2 | Phase 3 | Phase 4 |
| Corn | 854.15 | 1028.90 | 887.59 | 999.19 |
| Soybean meal | 350.00 | 450.00 | 635.02 | 412.75 |
| Distillers dried grains | — | — | 400.00 | 500.00 |
| Whey dried | 417.00 | 250.00 | — | — |
| Fish Meal-Menhaden | 96.00 | 42.00 | — | — |
| Soy protein | 150.00 | 100.00 | — | — |
| Blood plasma | 6.00 | 3.00 | — | — |
| Lysine HCL 78.8% | 5.60 | 6.50 | 8.28 | 13.36 |
| DL Methionine 99% | 3.05 | 2.80 | 1.14 | 2.06 |
| Threonine 98.5% | 2.20 | 2.10 | 2.20 | 3.97 |
| Tryptophan 100% | — | — | 0.20 | 1.07 |
| Monocalcium phosphate | 13.50 | 26.50 | 1.69 | — |
| Calcium Carbonate | 10.20 | 15.80 | 27.17 | 28.72 |
| Salt | 11.00 | 7.10 | 9.00 | 9.00 |
| Choline Chloride 60% | 1.00 | 1.00 | — | — |
| Vitamin/Trace Mineral Premix | 3.00 | 3.00 | 3.00 | 3.00 |
| Fat | 67.00 | 51.00 | 23.02 | 25.19 |
| Phytase | — | — | 0.35 | 0.35 |
| Hemicellulase | — | — | 0.50 | 0.50 |
| Tribasic Copper Chloride | — | — | 0.84 | 0.84 |
| Formulated yeast | 2.00 | 2.00 | — | — |
| Zinc oxide | 8.30 | 8.30 | — | — |
| Total, lb | 2000 | 2000 | 2000 | 2000 |

TABLE 6

Effects of feeding formulated yeast and Bacillus probiotic to sows on sow reproductive performance (values are least square means)[1]

| | No Yeast | | Yeast | | | P-values | | |
|---|---|---|---|---|---|---|---|---|
| Item | No Bacillus | Bacillus | No Bacillus | Bacillus | PSE | Yeast | Bacillus | Interaction |
| # Total Litters | 110 | 99 | 112 | 106 | x | x | x | x |
| Parity | 5.3 | 5.3 | 5.6 | 4.8 | 0.3 | 0.65 | 0.14 | 0.17 |
| Total born per litter | 14.1 | 14.3 | 14.9 | 14.6 | 0.4 | 0.07 | 0.85 | 0.35 |
| Born alive per litter | 13.2 | 13.4 | 13.7 | 13.4 | 0.4 | 0.32 | 0.89 | 0.28 |
| Stillborns, % | 3.5 | 3.2 | 4.0 | 3.7 | 0.7 | 0.47 | 0.63 | 0.99 |
| Mummies, % | 2.3 | 2.3 | 3.2 | 3.0 | 0.5 | 0.07 | 0.77 | 0.91 |
| Litter birth wt, lb | 37.9 | 38.6 | 39.1 | 38.6 | 1.7 | 0.48 | 0.88 | 0.42 |
| Pig birth wt (adj for born alive), lb | 2.88 | 2.89 | 2.88 | 2.89 | 0.07 | 1.00 | 0.77 | 0.98 |
| Pig wean wt (adj for lactation days), lb | 12.09 | 12.12(+0.2%) | 12.06(−0.2%) | 12.21(+1%) | 0.14 | 0.84 | 0.51 | 0.65 |

[1](Values) in parentheses indicate the percent increase or decrease relative to the Control pigs (No Yeast/No Bacillus)

TABLE 7

Effects of feeding a formulated yeast and Bacillus to sows on sow fecal measurements (values are least square means)

| | No Yeast | | Yeast | | | P-values | | |
|---|---|---|---|---|---|---|---|---|
| Item | No Bacillus | Bacillus | No Bacillus | Bacillus | PSE | Yeast | Bacillus | Interaction |
| Before farrowing | | | | | | | | |
| # of samples | 25 | 25 | 26 | 25 | x | x | x | x |
| E. coli, log CFU/g | 7.14 | 7.05 | 7.25 | 6.68 | 0.19 | 0.47 | 0.05 | 0.18 |
| % Difference vs. Control | | −1.3% | +1.5% | −6.4% | | | | |
| Clostridium, log CFU/g | 6.44 | 6.63 | 6.48 | 6.41 | 0.21 | 0.66 | 0.75 | 0.54 |
| MRS, log CFU/g | 8.01 | 7.59 | 7.88 | 8.01 | 0.24 | 0.47 | 0.45 | 0.16 |

TABLE 7-continued

Effects of feeding a formulated yeast and *Bacillus* to sows on sow fecal measurements (values are least square means)

| | No Yeast | | Yeast | | | P-values | | |
|---|---|---|---|---|---|---|---|---|
| Item | No *Bacillus* | *Bacillus* | No *Bacillus* | *Bacillus* | PSE | Yeast | *Bacillus* | Interaction |
| At wearing | | | | | | | | |
| # of samples | 11 | 13 | 14 | 14 | x | x | x | x |
| *E. coli*, log CFU/g | 6.82 | 6.69 | 6.90 | 6.33 | 0.43 | 0.70 | 0.32 | 0.56 |
| % Difference vs. Control | | −1.9% | +1.2% | −7.2% | | | | |
| *Clostridium*, log CFU/g | 4.93 | 5.01 | 5.70 | 5.54 | 0.27 | 0.008 | 0.85 | 0.62 |
| MRS, log CFU/g | 8.07 | 8.02 | 8.03 | 7.89 | 0.15 | 0.48 | 0.43 | 0.71 |

TABLE 8

Effects of feeding a formulated yeast and *Bacillus* probiotic to sows on immunological measurements (values are least square means)

| | No Yeast | | Yeast | | | P-values | | |
|---|---|---|---|---|---|---|---|---|
| Item | No *Bacillus* | *Bacillus* | No *Bacillus* | *Bacillus* | PSE | Yeast | *Bacillus* | Interaction |
| Immunological measurements of sows | | | | | | | | |
| # of sows | 24 | 22 | 23 | 23 | x | x | x | x |
| Serum IFN-γ, pg/ml | | | | | | | | |
| Prior to farrow | 34.4 | 36.9 | 15.8 | 22.0 | 9.7 | 0.08 | 6.63 | 0.85 |
| % Difference vs. Control | | +7.3% | −54.1% | −36.0% | | | | |
| At weaning | 23.7 | 24.7 | 14.7 | 18.6 | 7.7 | 0.31 | 0.74 | 0.84 |
| % Difference vs. Control | | +4.25 | −37.0% | −21.5% | | | | |
| Serum TNF-α, pg/ml | | | | | | | | |
| Prior to farrow | 8.2 | 9.6 | 4.8 | 8.9 | 3.3 | 0.53 | 0.37 | 0.69 |
| At weaning | 7.9 | 9.8 | 4.8 | 9.1 | 3.3 | 0.56 | 0.32 | 0.70 |
| Serum alpha-1-acid glycoprotein, μg/ml | | | | | | | | |
| Prior to farrow | 1201 | 1554 | 1176 | 1182 | 310 | 0.45 | 0.47 | 0.52 |
| % Difference vs. Control | | +29.4% | −2.1% | −1.6% | | | | |
| At weaning | 2292 | 1992 | 1966 | 1192 | 587 | 0.13 | 0.14 | 0.43 |
| % Difference vs. Control | | −13.1% | −14.2% | −48.0% | | | | |
| Immunological measurements of piglets | | | | | | | | |
| # of litters | 24 | 20 | 24 | 23 | x | x | x | x |
| Serum IFN-γ, pg/ml | | | | | | | | |
| At birth | 48.3 | 29.0 | 47.4 | 37.2 | 9.4 | 0.68 | 0.08 | 0.60 |
| At weaning | 18.9 | 25.9 | 14.1 | 17.4 | 5.4 | 0.20 | 0.29 | 0.71 |
| Serum TNF-α, pg/ml | | | | | | | | |
| At birth | 11.2 | 20.7 | 8.6 | 7.9 | 4.0 | 0.05 | 0.22 | 0.17 |
| % Difference vs. Control | | +84.8% | −23.2% | −29.5% | | | | |
| At weaning | 10.9 | 20.7 | 8.3 | 8.3 | 4.1 | 0.05 | 0.19 | 0.18 |
| % Difference vs. Control | | +15.0% | +8.1% | −6.8% | | | | |
| Serum alpha-1-acid glycoprotein, μg/ml | | | | | | | | |
| At birth | 10196[ab] | 10482[ab] | 11169[a] | 8534[b] | 801 | 0.52 | 0.11 | 0.05 |
| % Difference vs. Control | | −2.8% | −9.5% | −16.3% | | | | |
| At weaning | 5805 | 6673 | 6278 | 541.0 | 497 | 0.40 | 1.00 | 0.06 |
| % Difference vs. Control | | +15.0% | +8.1% | −6.8% | | | | |
| Serum immunocrit | | | | | | | | |
| At birth | 0.33 | 0.28 | 0.31 | 0.31 | 0.03 | 0.90 | 0.47 | 0.38 |
| At weaning | 0.10[a] | 0.11[ab] | 0.12[b] | 0.11[ab] | 0.01 | 0.10 | 0.59 | 0.02 |

[a,b]Means without a common superscript differ (P < 0.05)

TABLE 9

Effects of feeding a formulated yeast and *Bacillus* probiotic to sows on survivability of their offspring during the nursery phase of production (values are least square means).

| | No Yeast | | Yeast | | | P-value | | |
|---|---|---|---|---|---|---|---|---|
| Item | No *Bacillus* | *Bacillus* | No *Bacillus* | *Bacillus* | SE | Yeast | *Bacillus* | Interaction |
| Removals, % | 0.32 | 0.00 | 1.28 | 1.05 | x | 0.04 | 0.68 | x |
| | | | Phase 1 to 4; 51 days | | | | | |
| Days on experiment | 51.2 | 51.0 | 51.6 | 51.0 | x | x | x | x |
| Removals, % | 2.92 | 1.11 | 4.26 | 2.09 | x | 0.30 | 0.05 | x |

[1]Weaning BW was used as covariate when analyzing all responses
[2]Days on experiment was used as covariate when analyzing these responses
[a,b,c]Means without a common superscript differ (P < 0.05)

TABLE 10

Effects of feeding a formulated yeast and *Bacillus* probiotic to sows on fecal measurements of their offspring during the post-weaning nursery phase (values are least square means)

| | No Yeast | | Yeast | | | P-value | | |
|---|---|---|---|---|---|---|---|---|
| Item | No *Bacillus* | *Bacillus* | No *Bacillus* | *Bacillus* | SE | Yeast | *Bacillus* | Interaction |
| # of Pens | 13 | 11 | 9 | 11 | x | x | x | x |
| Post-weaning fecal score | | | | | | | | |
| Day 3 | 0.84 | 0.35 | 0.70 | 0.63 | 0.13 | 0.63 | 0.06 | 0.16 |
| Day 5 | 0.84 | 0.71 | 1.15 | 0.90 | 0.12 | 0.08 | 0.18 | 0.66 |
| Day 7 | 0.93 | 1.37 | 1.21 | 1.28 | 0.17 | 0.64 | 0.19 | 0.34 |
| Day 10 | 0.77 | 0.83 | 0.86 | 0.91 | 0.15 | 0.61 | 0.76 | 0.99 |
| Day 14 | 0.00 | 0.00 | 0.00 | 0.00 | | | | |
| | | | Fecal measurements of bacteria | | | | | |
| Day 3 | | | | | | | | |
| *E. coli*, log CFU/g | 8.48 | 8.44 | 8.00 | 8.39 | 0.12 | 0.05 | 0.19 | 0.11 |
| *Clostridium*, log CFU/g | 7.05 | 6.94 | 6.95 | 7.36 | 0.20 | 0.48 | 0.53 | 0.26 |
| Lactic acid bacteria, log CFU/g | $8.32^{ab}$ | $8.45^{ab}$ | $7.98^{a}$ | $8.67^{b}$ | 0.13 | 0.66 | 0.009 | 0.06 |

[a,b]Means without a common superscript differ (P < 0.05)

TABLE 11

Effects of feeding a formulated yeast and Bacillus probiotic to sows on immunological measurements of their offspring (values are least square means)

| | No Yeast | | Yeast | | | P-value | | |
|---|---|---|---|---|---|---|---|---|
| Item | No *Bacillus* | *Bacillus* | No *Bacillus* | *Bacillus* | SE | Yeast | *Bacillus* | Interaction |
| # of Pens | 13 | 11 | 9 | 11 | x | x | x | x |
| | | | Serum IFN-γ, pg/ml | | | | | |
| Weaning | 4.79 | 5.61 | 7.20 | 13.45 | 3.41 | 0.07 | 0.25 | 0.45 |
| % Difference vs. Control | | +17.1% | +50.3% | +180.8% | | | | |
| End of Phase 2 | 1.33 | 2.99 | 5.35 | 4.34 | 1.13 | 0.04 | 0.79 | 0.29 |
| End of Phase 4 | 1.56 | 3.10 | 5.66 | 4.30 | 1.34 | 0.06 | 0.95 | 0.30 |
| | | | Serum TNF-α, pg/ml | | | | | |
| Weaning | 3.91 | 6.54 | 3.26 | 7.76 | 1.96 | 0.97 | 0.02 | 0.55 |
| % Difference vs. Control | | +67.2% | −16.6% | +98.5% | | | | |
| End of Phase 2 | 1.75 | 2.82 | 2.73 | 6.20 | 1.77 | 0.27 | 0.25 | 0.54 |
| % Difference vs. Control | | +61.1% | +56.0% | +254.3% | | | | |
| End of Phase 4 | 2.11 | 0.41 | 3.75 | 2.62 | 1.45 | 0.21 | 0.35 | 0.85 |

TABLE 11-continued

Effects of feeding a formulated yeast and Bacillus probiotic to sows on immunological measurements of their offspring (values are least square means)

| | No Yeast | | Yeast | | | P-value | | |
|---|---|---|---|---|---|---|---|---|
| Item | No Bacillus | Bacillus | No Bacillus | Bacillus | SE | Yeast | Bacillus | Interaction |
| Serum alpha-1-acid glycoprotein, µg/ml | | | | | | | | |
| Weaning | 8133 | 7009 | 9366 | 6819 | 905 | 0.61 | 0.08 | 0.48 |
| End of Phase 2 | 2521 | 1887 | 2980 | 1961 | 529 | 0.61 | 0.09 | 0.75 |

Example 2

A Formulated Yeast and *Bacillus* Probiotic Administered to the Sow Alters the Microbial Ecology of Sows and Their Offspring A total of 500 sows were randomly assigned to one of four treatment groups and blocked based on parity. Detailed methods of this study are previously described in Example 1. Briefly, treatments administered to sows included 1) a control, basal diet; 2) *Bacillus subtilis* two-strain direct-fed microbial (DFM; *Bacillus subtilis* ABS1104 NRRL B-67258; *Bacillus subtilis* BS2084 NRRL B-50013); 3) formulated yeast containing yeast extract, hydrolyzed yeast, and yeast culture; or 4) *Bacillus* DFM+formulated yeast. Fecal samples were collected from 25 sows/treatment at the end of gestation and during the lactation phase, from pigs in the sows' litters at 5 days of age and 18 days of age, and from pigs during the post-weaning nursery phase at 24 days of age and 35 days of age. Microbial DNA was isolated from the fecal samples and the bacterial ecology was assessed by terminal restriction fragment length polymorphism (TRFLP) analysis.

DNA was extracted from fecal samples using the MoBio Powersoil DNA. Isolation kit (Mo Bio Laboratories, Carlsbad, Calif.) as per the manufacturer's instructions. The extracted DNA was further purified using the Zymo PCR inhibitor removal kit (Zymo Research, Irvine, Calif.). For each sample PCR amplification reactions were performed to amplify total bacterial 16S rRNA genes using the universal forward primer, 27F-YM, labeled with 6-carboxyfluorescein (FAM) and the universal reverse primer, 785R. The labeled polymerase chain reaction amplicons were purified using the Zymo DNA Clean & Concentrator™ kit. Purified bacteria DNA amplicons were digested using restriction enzymes HaeIII, and MspI.

Fragment detection was done at the University of Illinois, Urbana-Champaign Core DNA Sequencing Facility. Fragment analysis was performed with Genemapper 5 (Thermo Fisher Scientific, Waltham, Mass.). The resulting peak tables were imported into BioNumerics version 7.1 (Applied Maths, Sint-Martens-Lateen Belgium) for comparative analysis. Where possible putative identifications were made for TRFLP peaks to the lowest possible taxonomic level using the MiCA database (University of Idaho, Moscow, ID). Comparison of community composition and determination of the amount of variance attributable to treatment was performed using Canoco 5 (Microcomputer Power, Ithaca, N.Y.).

Principal component analysis revealed no differences in the fecal microbial ecology of sows during gestation (FIG. 1) or lactation (FIG. 2). Terminal restriction fragments (TRFs) indicating representative microbial members of the community are identified for gestation and lactation sows in Table 12 and Table 13, respectively. When analyzed by PCA, the microbial ecology of 5 day old pigs from sows fed the Yeast+*Bacillus* DFM treatment differed (P=0.10) compared to pigs from sows fed the other three treatments (FIG. 3). Several unidentifiable TRFs (235; 81) and TRFs identified as Enterobacteriaceae (249), *Bacillus* (334), *Bacillus subtilis* (225) and *Lactobacillus salivarius* (327) were present in 5 day old piglets at a much different proportions in the Yeast+*Bacillus* treatment than any of the others. (Table 14). No difference was observed for 18 day old piglets from sows fed any of the four treatments (FIG. 4; Table 15).

The microbial ecology of fecal samples collected from 24-day old weaned nursery pigs born to sows fed the Yeast-*Bacillus* DFM treatment was different (P=0.1.1) from pigs born to sows fed the other three treatments (FIG. 5). Unidentifiable TRFs (276) and TRFs identified as Clostridiales (265) and Bacteroides (255) were present in 24 day old post-weaning nursery pigs at a much different proportions in the Yeast+*Bacillus* treatment than any of the others. (Table 16). The fecal microbial ecology of 35-day old weaned nursery pigs born to sows fed the Yeast treatment differed (P=0,01) from the other three treatments (FIG. 6); however, many TRFs were present in much lower proportions in the Yeast+*Bacillus* treatment than any of the others, such as several unidentifiable TRFs (81, 239, 321), *Lactobacillus crispatus* (272), and *Lactobacillus* sp. (288).

TABLE 12

The proportion of terminal restriction fragments (TRFs) as a percentage based on total peak height, in the fecal communities of gestating sows, as well as putative taxonomic identification of those TRFs.

| TRF | IDENTIFICATION | CONTROL | DFM | YEAST | YEAST + DFM |
|---|---|---|---|---|---|
| 31 | Unidentified | 16.5 | 12.9 | 12.1 | 18.5 |
| 245 | Bacteroides | 1.9 | 2.4 | 1.7 | 1.5 |
| 272 | L. crispatus | 3.7 | 4.7 | 3.3 | 3.5 |
| 265 | Clostridiales | 2.1 | 2.4 | 3.0 | 2.6 |
| 235 | Unidentified | 6.0 | 7.1 | 6.1 | 4.5 |
| 259 | Unidentified | 4.6 | 5.2 | 5.7 | 5.9 |
| 262 | Clostridium | 3.6 | 4.2 | 3.7 | 4.6 |
| 255 | Bacteroides | 5.6 | 7.0 | 5.6 | 6.8 |
| 317 | Veillonellaceae | 3.7 | 3.7 | 2.7 | 3.6 |
| 288 | Lactobacillus sp. | 5.1 | 4.7 | 6.5 | 5.0 |
| 61 | Unidentified | 0.8 | 1.0 | 1.2 | 1.0 |
| 276 | Unidentified | 2.3 | 3.3 | 2.8 | 2.8 |
| 221 | Clostridium | 4.5 | 3.9 | 5.0 | 3.5 |
| 81 | Unidentified | 0.7 | 1.0 | 1.0 | 1.0 |
| 249 | Enterobacteriaceae | 2.0 | 0.9 | 2.0 | 1.3 |
| 239 | Unidentified | 2.8 | 2.6 | 3.5 | 2.9 |
| 299 | Unidentified | 3.7 | 3.4 | 3.9 | 3.2 |
| 321 | Unidentified | 2.4 | 2.9 | 2.5 | 3.7 |
| 293 | Unidentified | 3.6 | 5.6 | 4.0 | 2.5 |
| 303 | Unidentified | 2.0 | 2.2 | 2.3 | 1.6 |
| 281 | Unidentified | 2.6 | 1.7 | 1.7 | 2.1 |
| 158 | Unidentified | 3.8 | 3.8 | 2.7 | 3.7 |

TABLE 12-continued

The proportion of terminal restriction fragments (TRFs) as a percentage based on total peak height, in the fecal communities of gestating sows, as well as putative taxonomic identification of those TRFs.

| TRF | IDENTIFICATION | CONTROL | DFM | YEAST | YEAST + DFM |
|---|---|---|---|---|---|
| 307 | Unidentified | 1.6 | 1.0 | 1.6 | 0.9 |
| 334 | *Bacillus* | 1.0 | 1.2 | 1.3 | 0.7 |
| 225 | *Bacillus subtilis* | 2.5 | 1.5 | 2.4 | 1.6 |
| 327 | *L. salivarius* | 0.8 | 0.9 | 0.9 | 0.8 |
|  | Minor Peaks | 10.0 | 8.5 | 10.9 | 10.4 |

TABLE 13

The proportion of terminal restriction fragments (TRFs) as a percentage based on total peak height, in the fecal communities of lactating sows, as well as putative taxonomic identification of those TRFs.

| TRF | IDENTIFICATION | CONTROL | DFM | YEAST | YEAST + DFM |
|---|---|---|---|---|---|
| 31 | Unidentified | 8.2 | 8.4 | 11.7 | 8.1 |
| 245 | Bacteroides | 2.7 | 1.9 | 1.2 | 3.2 |
| 272 | *L. crispatus* | 4.0 | 3.1 | 3.7 | 3.1 |
| 265 | *Clostridiales* | 3.6 | 4.2 | 3.1 | 3.5 |
| 235 | Unidentified | 5.5 | 7.5 | 6.2 | 5.4 |
| 259 | Unidentified | 5.2 | 5.1 | 4.7 | 6.8 |
| 262 | *Clostridium* | 4.0 | 3.3 | 3.3 | 5.1 |
| 255 | Bacteroides | 6.2 | 4.8 | 7.6 | 5.6 |
| 317 | *Veillonellaceae* | 2.8 | 2.6 | 3.7 | 3.4 |
| 288 | *Lactobacillus* sp. | 12.7 | 7.9 | 8.3 | 9.4 |
| 61 | Unidentified | 1.5 | 1.3 | 1.5 | 1.4 |
| 276 | Unidentified | 1.5 | 1.5 | 2.3 | 2.8 |
| 221 | *Clotridium* | 3.3 | 3.8 | 4.7 | 4.4 |
| 81 | Unidentified | 1.3 | 3.5 | 1.3 | 1.3 |
| 249 | *Enterobacteriaceae* | 2.1 | 1.5 | 1.3 | 0.5 |
| 239 | Unidentified | 2.0 | 1.3 | 1.1 | 1.7 |
| 299 | Unidentified | 3.6 | 2.7 | 3.1 | 3.4 |
| 321 | Unidentified | 2.9 | 3.0 | 3.9 | 2.7 |
| 293 | Unidentified | 1.7 | 4.4 | 4.1 | 4.3 |
| 303 | Unidentified | 1.1 | 4.2 | 2.1 | 1.8 |
| 281 | Unidentified | 2.1 | 2.7 | 1.7 | 1.7 |
| 158 | Unidentified | 1.1 | 1.2 | 0.4 | 1.3 |
| 307 | Unidentified | 2.0 | 1.5 | 1.4 | 1.3 |
| 334 | *Bacillus* | 2.4 | 1.5 | 1.4 | 1.0 |
| 225 | *Bacillus subtilis* | 4.7 | 2.6 | 1.6 | 2.9 |
| 327 | *L. salivarius* | 0.9 | 1.3 | 1.0 | 1.0 |
|  | Minor Peaks | 10.8 | 13.0 | 13.2 | 11.3 |

TABLE 14

The proportion of terminal restriction fragments (TRFs), as a percentage based on total peak height, in the fecal communities of 5 day old piglets, as well as putative taxonomic identification of those TRFs.

| TRF | IDENTIFICATION | CONTROL | DFM | YEAST | YEAST + DFM |
|---|---|---|---|---|---|
| 31 | Unidentified | 13.8 | 8.3 | 19.6 | 8.6 |
| 245 | Bacteroides | 6.6 | 4.4 | 2.8 | 5.0 |
| 272 | *L. crispatus* | 11.0 | 7.5 | 11.8 | 8.7 |
| 265 | *Clostridiales* | 8.5 | 7.9 | 3.5 | 4.6 |
| 235 | Unidentified | 0.2 | 1.2 | 0.6 | 3.8 |
| 259 | Unidentified | 1.0 | 7.1 | 1.6 | 1.6 |
| 262 | *Clostridium* | 2.2 | 5.2 | 6.7 | 6.5 |
| 255 | Bacteroides | 3.1 | 3.3 | 1.8 | 1.5 |
| 317 | *Veillonellaceae* | 1.5 | 3.1 | 2.1 | 3.2 |
| 288 | *Lactobacillus* sp. | 1.6 | 0.8 | 1.2 | 1.4 |
| 61 | Unidentified | 1.2 | 2.5 | 0.6 | 1.4 |
| 276 | Unidentified | 2.0 | 5.1 | 3.7 | 3.6 |
| 221 | *Clostridium* | 0.6 | 0.7 | 3.8 | 1.5 |

TABLE 14-continued

The proportion of terminal restriction fragments (TRFs), as a percentage based on total peak height, in the fecal communities of 5 day old piglets, as well as putative taxonomic identification of those TRFs.

| TRF | IDENTIFICATION | CONTROL | DFM | YEAST | YEAST + DFM |
|---|---|---|---|---|---|
| 81 | Unidentified | 13.0 | 9.6 | 7.8 | 3.2 |
| 249 | *Enterobacteriaceae* | 3.3 | 3.0 | 6.8 | 13.5 |
| 239 | Unidentified | 0.0 | 1.5 | 2.0 | 0.8 |
| 299 | Unidentified | 0.6 | 2.7 | 0.9 | 0.9 |
| 321 | Unidentified | 0.9 | 2.6 | 1.8 | 1.1 |
| 293 | Unidentified | 0.2 | 1.1 | 0.7 | 0.5 |
| 303 | Unidentified | 2.4 | 1.5 | 0.1 | 1.0 |
| 281 | Unidentified | 5.8 | 1.0 | 1.6 | 3.9 |
| 158 | Unidentified | 0.9 | 1.5 | 0.5 | 0.6 |
| 307 | Unidentified | 3.5 | 0.8 | 1.6 | 1.5 |
| 334 | *Bacillus* | 0.4 | 0.5 | 0.8 | 1.9 |
| 225 | *Bacillus subtilis* | 0.1 | 0.1 | 0.1 | 0.4 |
| 327 | *L. salivarius* | 0.2 | 0.2 | 0.7 | 2.3 |
|  | Minor Peaks | 15.4 | 16.9 | 14.5 | 17.0 |

TABLE 15

The proportion of terminal restriction fragments (TRFs) as a percentage based on total peak height, in the fecal communities of 18 day old piglets, as well as putative taxonomic identification of those TRFs.

| TRF | IDENTIFICATION | CONTROL | DFM | YEAST | YEAST + DFM |
|---|---|---|---|---|---|
| 31 | Unidentified | 6.8 | 13.3 | 21.0 | 9.5 |
| 245 | Bacteroides | 3.5 | 8.2 | 6.7 | 3.6 |
| 272 | *L. crispatus* | 7.0 | 9.4 | 7.2 | 8.5 |
| 265 | *Clostridiales* | 7.8 | 4.6 | 4.7 | 4.4 |
| 235 | Unidentified | 4.7 | 7.8 | 3.9 | 4.8 |
| 259 | Unidentified | 5.1 | 2.2 | 4.6 | 3.7 |
| 262 | *Clostridium* | 5.5 | 7.5 | 5.6 | 5.3 |
| 255 | Bacteroides | 3.3 | 1.1 | 2.8 | 1.8 |
| 317 | *Veillonellaceae* | 6.5 | 2.7 | 5.3 | 5.9 |
| 288 | *Lactobacillus* sp. | 2.0 | 0.8 | 1.1 | 0.8 |
| 61 | Unidentified | 3.4 | 2.0 | 2.2 | 4.3 |
| 276 | Unidentified | 2.9 | 1.0 | 1.5 | 6.3 |
| 221 | *Clostridium* | 1.6 | 1.2 | 4.5 | 1.5 |
| 81 | Unidentified | 4.9 | 2.6 | 2.7 | 4.6 |
| 249 | *Enterobacteriaceae* | 0.6 | 4.6 | 0.4 | 2.6 |
| 239 | Unidentified | 5.2 | 2.0 | 4.3 | 4.2 |
| 299 | Unidentified | 1.7 | 2.8 | 2.0 | 1.8 |
| 321 | Unidentified | 1.3 | 1.4 | 0.5 | 0.7 |
| 293 | Unidentified | 1.3 | 1.9 | 0.9 | 0.7 |
| 303 | Unidentified | 2.8 | 1.1 | 3.2 | 2.1 |
| 281 | Unidentified | 1.9 | 0.2 | 0.2 | 1.8 |
| 158 | Unidentified | 1.0 | 0.4 | 0.3 | 0.4 |
| 307 | Unidentified | 1.3 | 0.9 | 0.9 | 1.0 |
| 334 | *Bacillus* | 1.1 | 0.3 | 1.5 | 1.0 |
| 225 | *Bacillus subtilis* | 0.2 | 0.1 | 0.1 | 0.3 |
| 327 | *L. salivarius* | 0.1 | 1.4 | 0.4 | 2.9 |
|  | Minor Peaks | 16.6 | 18.6 | 11.4 | 15.5 |

TABLE 16

The proportion of terminal restriction fragments (TRFs) as a percentage based on total peak height, in the fecal communities of 24 day old nursery pigs, as well as putative taxonomic identification of those TRFs.

| TRF | IDENTIFICATION | CONTROL | DFM | YEAST | YEAST + DFM |
|---|---|---|---|---|---|
| 31 | Unidentified | 21.3 | 17.8 | 26.7 | 13.7 |
| 245 | Bacteroides | 0.9 | 1.1 | 1.8 | 1.2 |
| 272 | *L. crispatus* | 5.9 | 7.9 | 6.7 | 7.5 |
| 265 | *Clostridiales* | 5.5 | 5.7 | 5.1 | 6.2 |

TABLE 16-continued

The proportion of terminal restriction fragments (TRFs) as a percentage based on total peak height, in the fecal communities of 24 day old nursery pigs, as well as putative taxonomic identification of those TRFs.

| TRF | IDENTIFICATION | CONTROL | DFM | YEAST | YEAST + DFM |
|---|---|---|---|---|---|
| 235 | Unidentified | 5.1 | 8.3 | 9.2 | 8.4 |
| 259 | Unidentified | 4.8 | 6.1 | 5.5 | 6.0 |
| 262 | Clostridium | 3.4 | 2.1 | 4.4 | 3.1 |
| 255 | Bacteroides | 3.2 | 3.8 | 0.9 | 5.3 |
| 317 | Veillonellaceae | 6.1 | 11.0 | 2.8 | 4.9 |
| 288 | Lactobacillus sp. | 0.4 | 0.7 | 1.2 | 0.8 |
| 61 | Unidentified | 1.0 | 1.4 | 0.3 | 1.4 |
| 276 | Unidentified | 5.0 | 5.7 | 2.1 | 1.5 |
| 221 | Clostridium | 0.3 | 0.4 | 0.1 | 0.8 |
| 81 | Unidentified | 1.6 | 1.7 | 4.9 | 3.1 |
| 249 | Enterobacteriaceae | 0.7 | 1.0 | 0.8 | 1.1 |
| 239 | Unidentified | 6.2 | 0.6 | 1.8 | 2.7 |
| 299 | Unidentified | 2.1 | 1.4 | 1.2 | 2.1 |
| 321 | Unidentified | 0.5 | 1.4 | 3.5 | 0.6 |
| 293 | Unidentified | 0.1 | 0.2 | 1.8 | 0.4 |
| 303 | Unidentified | 3.3 | 3.1 | 2.8 | 2.3 |
| 281 | Unidentified | 1.5 | 1.0 | 0.2 | 0.7 |
| 158 | Unidentified | 0.0 | 0.2 | 0.1 | 0.0 |
| 307 | Unidentified | 0.7 | 0.9 | 0.8 | 0.7 |
| 334 | Bacillus | 0.5 | 0.3 | 0.1 | 0.2 |
| 225 | Bacillus subtilis | 0.0 | 0.2 | 0.0 | 0.1 |
| 127 | L. salivarius | 0.9 | 0.2 | 0.1 | 0.6 |
| | Minor Peaks | 18.6 | 15.6 | 15.1 | 24.2 |

TABLE 17

The proportion of terminal restriction fragments (TRFs) as a percentage based on total peak height, in the fecal communities of 35 day old nursery pigs, as well as putative taxonomic identification of those TRFs.

| TRF | IDENTIFICATION | CONTROL | DFM | YEAST | YEAST + DFM |
|---|---|---|---|---|---|
| 31 | Unidentified | 1.0 | 1.7 | 1.1 | 1.8 |
| 245 | Bacteroides | 22.4 | 16.3 | 33.7 | 20.6 |
| 272 | L. crispatus | 6.1 | 3.3 | 4.2 | 2.8 |
| 265 | Clostridiales | 7.1 | 10.7 | 6.9 | 9.7 |
| 235 | Unidentified | 3.0 | 1.5 | 2.6 | 1.3 |
| 259 | Unidentified | 2.2 | 4.3 | 2.1 | 2.5 |
| 262 | Clostridium | 2.6 | 3.8 | 1.8 | 3.4 |
| 255 | Bacteroides | 0.9 | 1.4 | 0.7 | 1.4 |
| 317 | Veillonellaceae | 2.5 | 2.1 | 1.8 | 1.9 |
| 288 | Lactobacillus sp. | 1.2 | 1.3 | 1.1 | 0.9 |
| 61 | Unidentified | 12.5 | 13.9 | 13.0 | 12.5 |
| 276 | Unidentified | 5.9 | 4.7 | 5.7 | 6.5 |
| 221 | Clostridium | 1.0 | 3.0 | 1.9 | 2.1 |
| 81 | Unidentified | 2.0 | 1.5 | 0.8 | 0.3 |
| 249 | Enterobacteriaceae | 1.8 | 5.6 | 0.0 | 5.7 |
| 239 | Unidentified | 1.9 | 2.8 | 1.2 | 0.6 |
| 299 | Unidentified | 0.9 | 1.4 | 1.3 | 1.2 |
| 321 | Unidentified | 3.7 | 2.1 | 2.2 | 1.7 |
| 293 | Unidentified | 1.3 | 0.6 | 0.5 | 0.4 |
| 303 | Unidentified | 1.3 | 0.6 | 0.7 | 1.3 |
| 281 | Unidentified | 0.3 | 0.0 | 0.1 | 0.0 |
| 158 | Unidentified | 0.6 | 1.4 | 0.6 | 1.0 |
| 307 | Unidentified | 2.0 | 1.6 | 2.2 | 1.5 |
| 334 | Bacillus | 2.1 | 1.9 | 2.9 | 3.1 |
| 225 | Bacillus subtilis | 0.3 | 0.2 | 1.0 | 0.8 |
| 327 | L. salivarius | 1.9 | 2.2 | 2.9 | 2.1 |
| | Minor Peaks | 11.6 | 10.2 | 6.8 | 12.8 |

It should be understood that the above description, while indicating representative embodiments of the present invention, is given by way of illustration and not of limitation, Many changes and modifications may be made within the scope of the present invention without departing from the spirit thereof, and the invention includes all such modifications.

Various additions, modifications and rearrangements are contemplated as being within the scope of the following claims, which particularly point out and distinctly claim the subject matter regarded as the invention, and it is intended that the following claims cover all such additions, modifications and rearrangements.

BIBLIOGRAPHY

Baker, A. A., E. Davis, J. D. Spencer, R. Moser, and T. Rehberger. 2013. The effect of a Bacillus-based direct-fed microbial supplemented to sows on the gastrointestinal microbiota of their neonatal piglets. J. Anim. Sci. 91:3390-3399.

Barker, M. R., S. S. Britz, J. C, Nietfeld, and S. E. Minton. 2003. Effects of BioPlus 2B and Levucell SB on weanling pig growth performance and fecal shedding in response to oral challenge with Salmonella serovar Typhimuruim. Proceedings of the Kansas State University Swine Day 2003. pp. 136-140.

Bass, B., V. Perez, H. Yang, D. Holzgraefe, J, Chewning, and C. Maxwell, 2012. Impact of a whole yeast product on sow, litter, and nursery performance. Arkansas Anim Sci Dep Rep 1: 104-115.

Chen, Y. S., B. J. Min, J. H. Cho, O. S. Kwon, K. S. Son, H. J. Kim, and I. H. Kim. 2006, Effects of dietary Bacillus-based probiotic on growth perfbrmance, nutrients digestibility, blood characteristics and fecal noxious gas content in finishing pigs. Asian-Aust. J. Anim. Sci. 4:587-592.

Choi, J. Y., P. L. Shinde, S. L. Ingale, J. S. Kim, K. H. Kim, T. K. Kwon, and B. J. Chae. 2011. Evaluation of multi-microbe probiotics prepared by submerged liquid or solid state fermentation and antibiotics in weaning pigs, Livestock Sci. 138:144-151.

Cui, C., C. J. Shen, G. Jia, and K. N, Wang. 2013. Effects of dietary Bacillus subtilis on proportion of Bacteroidetes and Firmicutes in swine intestine and lipid metabolism. Genetics and Molecular Research, 12:1766-1776.

Davis, M. E., T. Parrott, D. C. Brown, B. Z. de Rodas, Z. B. Johnson, C. V. Maxwell, and T. Rehberger, 2008. Effect of a Bacillus-based direct-fed microbial feed supplement on growth performance and pen cleaning characteristics of growing-finishing pigs. J. Anim. Sci. 86: 1459-1467.

Fahrny, M. H. and C. S. Bernard, 1971. Interreations between some reproductive traits in swine. Can. J. Anim. Sci. 52:39-45.

Guiliano Z. F. Meurens, D. Serreau, C. Chevaleyre, S. Melo, M. Berri, R. D'Inca, E. Auclair, H. Salmon. 2012. Effects of dietary yeast strains on immunoglobulin in colostrum and milk of sows. Vet. Immunology and Immunopathology, 152:20-27.

Giang, H. H., T. Q. Viet, B. Ogle, and J. E. Lindberg. 2011, Effects of supplementation of probiotics on the performance, nutrient digestibility and faecal microflora in growing-finishing pigs. Asian-Aust. S. Anim. Sci. 24:655-661.

Gomez, S., M. L. Angeles, M. C, Mojica, and S. Jalukar. 2012. Combination of an enzymatically hydrolyzed yeast and yeast culture with a direct-fed microbial in the feeds of broiler chickens. Asian-Aust Anim. Sci. 25:665-673.

Hentges, D. J. 1992, but flora in disease resistance. P.87-110. in Probiotics: The scientific basis, Fuller, R., ed. Chapman and Hall, London, UK.

Hong, H. A., I. H. Due, and S. M. Cutting. 2005. The use of bacterial spore formers as probiotics FEMS Microbiology Reviews 29:813-835.

Hu, Y., Y. Dun, S. Li, S. Zhao, N. Peng, and Y, Liang, 2014. Effects of *Bacillus subtilis* KN-42 on growth performance, diarrhea and faecal bacterial flora of weaned piglets. Asian-Aust. J. Anim. Sci. 27:1131-1140.

Jang, Y. D., K. W. Kang, Piao, T. S. Jeong, E. Auclair, S. Jonvel, R. D'Inca and Y. Y. Kim. 2013. Effects of live yeast supplementation to gestation and lactation diets on reproductive performance, immunological parameters and milk composition in sows, Livestock Sci. 152:167-173.

Jurgers, M. H., R. A, Rikabi, and D. R. Zimmerman. 1997. The effect of dietary active dry yeast supplement on performance of sows during gestation-lactation and their pin. J. Anim. Sci. 75:593-597.

Kim, S. W., Brandherm, M., Newton, B., Cook, D. R., Yoon, I., & Fitzner, G. 2010. Effect of supplementing *Saccharomyces cerevisiae* fermentation product in sow diets on reproductive performance in a commercial environment, Canadian journal of animal science. 90: 229-232.

Lindemann, M. D., I. Hung, and G. L. Cromwell, 2010. Benefits of Cel-Can®, an enzymatically hydrolyzed yeast product, for sows and weanling pigs. American Association of Swine Veterinarians.

Maruta, K., H. Miyazaki, Y. Takada, S. Masuda, A. Suzuki, H. Takahashi, and Takahashi. 1996, Effects of *Bacillus subtilis* C-3102 intake on fecal flora of sows and on diarrhea and mortality rate of their piglets. Anim. Sci, Technol. 67:403-.409.

Min, B. J., O. S. Kwon, K. S. Son, J. H. Cho, W. B. Lee, J. H. Kim, B. C. Park, and I. H. Kim. 2003. The effect of *Bacillus* and active yeast complex supplementation on the performance, fecal *Bacillus* counts and ammonia nitrogen concentrations in weaned pigs. J. Anim. Sci. 82(Supp.1): 26 (abstract).

Plante, P. A., J-.P. Laforest, and C. Farmer. 2011. Effect of supplementing the diet of lactating sows with NuPro® on sow lactation performance and piglet growth. Canadian Journal of Animal Science 91: 295-300.

Soccol, C. R, L. P. de Souza Vandenberghe, M. R. Spier, A. B. P. Medeiros, C. T. Yamagushi, J. D, Lindner, A. Pandey, and V. Thomaz-Soccol. 2010. The potential of probiotics:a review. Food Technol. Biotechnol. 48:413-434.

Veum, T. L., J, Reyes and M. Ellersieck, 1995. Effect of supplemental yeast culture in sow gestation and lactation diets on apparent nutrient digestibilities and reproductive performance through one reproductive cycle. J. Anim. Sci. 73:1741-1745.

We claim:

1. A composition comprising:
a culture of one or more *Bacillus* strains comprising *Bacillus subtilis* 1104; and at least one of
a *Saccharomyces cerevisiae* yeast extract, a hydrolyzed *Saccharomyces cerevisiae* yeast, and a *Saccharomyces cerevisiae* yeast culture.

2. The composition of claim 1, further comprising a carrier.

3. The composition of claim 2, wherein the carrier is selected from a group consisting of: whey, maltodextrin, sucrose, dextrose, limestone, rice hulls, and sodium silica aluminate.

4. The composition of claim 1, wherein the *Saccharomyces cerevisiae* yeast product further comprises between 25 and 80 percent by weight of the *Saccharomyces cerevisiae* yeast extract, between 5 and 40 percent by weight of the hydrolyzed *Saccharomyces cerevisiae* yeast, and between 5 and 50 percent by weight of the *Saccharomyces cerevisiae* yeast culture.

5. The composition of claim 1, wherein the culture of one or more *Bacillus* strains is a direct fed microbial product.

6. The composition of claim 1, wherein the composition further comprises an animal feed.

7. The composition of claim 6, wherein the composition has a concentration of the culture of one or more *Bacillus* strains in the composition of about between 1×10e4 and 1×10e9 CFU/g of feed.

8. The composition of claim 7, wherein the composition in an animal feed is configured to be consumed by an animal and result in a concentration of the culture of one or more *Bacillus* strains introduced into the animal in the range of about between 1×10e5 and 1×10e11 CFU/g of feed.

9. The composition of claim 1, wherein the composition is a direct fed microbial composition comprising the culture of one or more *Bacillus* strains and an isolated *Saccharomyces cerevisiae* yeast product, and wherein the direct fed microbial composition inhibits *Escherichia coli* in a gastrointestinal tract of a swine having ingested an effective amount of said direct fed microbial composition.

10. A method of increasing the performance of a swine comprising administering to the swine an effective amount of a composition comprising a culture of one or more *Bacillus* strains comprising at least *Bacillus subtilis* 1104 and a *Saccharomyces cerevisiae* yeast product, wherein said *Saccharomyces cerevisiae* yeast product comprises at least one of a *Saccharomyces cerevisiae* yeast extract, a hydrolyzed *Saccharomyces cerevisiae* yeast, and a *Saccharomyces cerevisiae* yeast culture.

11. The method of increasing the performance of the swine of claim 10, further comprising improving immune system function in the swine.

12. The method of increasing the performance of the swine of claim 10, further comprising increasing immunoglobulins in the swine.

13. The method of increasing the performance of the swine of claim 10, further comprising reducing inflammation in the swine.

14. The method of increasing the performance of the swine of claim 10, further comprising improving survivability of a group of the swine.

15. The method of increasing the performance of the swine of claim 10, further comprising reducing mortality rate of a group of the swine.

16. The method of increasing the performance of the swine of claim 10, further comprising increasing interferon gamma in the swine.

17. The method of increasing the performance of the swine of claim 10, further comprising reduced day three scours post-weaning.

18. The method of increasing the performance of the swine of claim 17, further providing improved transition from a milk-based diet to a solid diet of the swine.

19. The method of increasing the performance of the swine of claim 10, further providing improved survivability of the swine post weaning.

20. The method of increasing the performance of the swine of claim 10, wherein the swine is a sow and the method further comprises providing increasing litter weaning weight in a litter born to the sow.

21. The method of increasing the performance of the swine of claim 10, wherein the swine is a sow and the method further comprises providing an increased number of live birth pigs born to the sow.

22. The method of increasing the performance of the swine of claim 10, further providing reduced pathogenic bacteria counts in the gut of the swine.

23. The method of increasing the performance of the swine of claim 10, wherein the swine is a sow and wherein increasing the performance of the swine further comprises positively managing gut health in the sow and an offspring of the sow throughout swine production phases.

24. The method of increasing the performance of the swine of claim 10, further comprising improving immune system function in an offspring born to the swine, wherein the swine is a sow having been administered an effective amount of the composition.

25. The method of claim 24, wherein the improved immune system function in the offspring born to the swine are selected from the group comprising at least one of: increasing immunoglobulins in the offspring, increasing interferon gamma in the offspring, reducing inflammation in the offspring, reducing day three scours post-weaning in the offspring, improved transition from a milk based diet to a solid diet of the offspring, increasing litter weaning weight of the offspring, improving survivability of a group of the offspring, improving survivability the group of the offspring post weaning, and reducing mortality rate of the group of the offspring.

26. The method of increasing the performance of the swine of claim 10, comprising administering a *Saccharomyces cerevisiae* yeast product.

27. The method of claim 10, wherein the composition comprising the culture of one or more *Bacillus* strains and the *Saccharomyces cerevisiae* yeast product are administered sequentially.

28. The method of claim 10, wherein the composition comprising the culture of one or more *Bacillus* strains and the *Saccharomyces cerevisiae* yeast product are administered concurrently.

29. The method of claim 28, wherein the composition comprises the culture of one or more *Bacillus* strains and the *Saccharomyces cerevisiae* yeast product.

30. The composition of claim 1, further comprising a culture of *Bacillus subtilis* 2084.

31. The method of increasing the performance of a swine according to claim 10, wherein the composition further comprises a culture of *Bacillus subtilis* 2084.

* * * * *